(12) United States Patent
Medintz et al.

(10) Patent No.: US 7,927,547 B2
(45) Date of Patent: Apr. 19, 2011

(54) REAGENTLESS AND REUSABLE BIOSENSORS WITH TUNABLE DIFFERENTIAL BINDING AFFINITIES AND METHODS OF MAKING

(75) Inventors: Igor L Medintz, Alexandria, VA (US); J Matthew Mauro, Eugene, OR (US); Ellen R Goldman, Germantown, MD (US); George P Anderson, Seabrook, MD (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 401 days.

(21) Appl. No.: 12/103,778

(22) Filed: Apr. 16, 2008

(65) Prior Publication Data
US 2009/0048123 A1     Feb. 19, 2009

Related U.S. Application Data

(62) Division of application No. 11/094,540, filed on Mar. 25, 2005, now Pat. No. 7,435,386.

(60) Provisional application No. 60/559,287, filed on Mar. 24, 2004.

(51) Int. Cl.
*G01N 21/00* (2006.01)
*G01N 21/01* (2006.01)
*G01N 21/64* (2006.01)
*G01N 33/53* (2006.01)
*G01N 33/553* (2006.01)

(52) U.S. Cl. ............... 422/82.08; 422/82.05; 422/82.06; 422/82.07; 435/6; 435/7.1; 435/7.5; 436/172

(58) Field of Classification Search .................. None
See application file for complete search history.

(56) References Cited

U.S. PATENT DOCUMENTS

| 4,868,103 | A | * | 9/1989 | Stavrianopoulos et al. | ...... 435/5 |
| 5,194,393 | A | * | 3/1993 | Hugl et al. | ...... 436/525 |
| 2002/0012951 | A1 | * | 1/2002 | Strittmatter | ...... 435/7.8 |

OTHER PUBLICATIONS

Medintz et al., "A fluorescence resonance energy transfer sensor based on maltose binding protein", Bioconjugate Chem., 2003, vol. 14, pp. 909-918.*

* cited by examiner

*Primary Examiner* — Unsu Jung
(74) *Attorney, Agent, or Firm* — Amy Ressing; Roy Roberts

(57) ABSTRACT

The biosensor comprises a modular biorecognition element and a modular flexible arm element. The biorecognition element and the flexible arm element are each labeled with a signaling element. The flexible arm contains an analog of an analyte of interest that binds with the biorecognition element, bringing the two signaling elements in close proximity, which establishes a baseline fluorescence resonance energy transfer (FRET). When an analyte of interest is provided to the biosensor, the analyte will displace the analyte analog, and with it, the signaling module of the modular flexible arm, causing a measurable change in the FRET signal in a analyte concentration dependent manner. The modularity of different portions of the biosensor allows functional flexibility. The biosensor operates without additional development reagents, requiring only the presence of analyte or target for function.

20 Claims, 8 Drawing Sheets

SEQUENCE LISTING

<160> NUMBER OF SEQ ID NOS: 12

<210> SEQ ID NO 1
<211> LENGTH: 378
<212> TYPE: PRT
<213> ORGANISM: Escherichia coli

<400> SEQUENCE: 1

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Lys
        355                 360                 365

Leu Thr Lys Gly Ser His His His His His
    370                 375

<210> SEQ ID NO 2
<211> LENGTH: 16
<212> TYPE: PRT
<213> ORGANISM: Artificial
<220> FEATURE:
<223> OTHER INFORMATION: Designed DNA sequence, does not originate
      from an organism

<400> SEQUENCE: 2

Ala Thr Ala Cys Cys Gly Thr Thr Cys Gly Cys Gly Cys Cys Cys Gly
1               5                   10                  15

<210> SEQ ID NO 3
<211> LENGTH: 24
<212> TYPE: PRT
<213> ORGANISM: Artificial
<220> FEATURE:
<223> OTHER INFORMATION: Designed DNA sequence, does not originate
      from an organism

<400> SEQUENCE: 3

Ala Cys Thr Gly Ala Cys Thr Gly Cys Gly Gly Gly Cys Gly Cys Gly
1               5                   10                  15

Ala Ala Cys Gly Gly Thr Ala Thr
            20

<210> SEQ ID NO 4
<211> LENGTH: 34
<212> TYPE: PRT
<213> ORGANISM: Artificial
<220> FEATURE:
<223> OTHER INFORMATION: Designed DNA sequence, does not originate
      from an organism

<400> SEQUENCE: 4

Ala Cys Thr Gly Ala Cys Thr Gly Gly Ala Ala Thr Cys Thr Gly Ala
1               5                   10                  15

Ala Thr Cys Gly Gly Gly Cys Gly Cys Gly Ala Ala Cys Gly Gly Thr
            20                  25                  30

Ala Thr

<210> SEQ ID NO 5
<211> LENGTH: 44
<212> TYPE: PRT
<213> ORGANISM: Artificial
<220> FEATURE:
<223> OTHER INFORMATION: Designed DNA sequence, does not originate
      from an organism

<400> SEQUENCE: 5

Ala Cys Thr Gly Ala Cys Thr Gly Thr Ala Cys Gly Ala Gly Thr Thr
1               5                   10                  15

Gly Ala Gly Ala Ala Thr Cys Thr Gly Ala Ala Thr Cys Gly Gly Gly
            20                  25                  30

Cys Gly Cys Gly Ala Ala Cys Gly Gly Thr Ala Thr
        35                  40

<210> SEQ ID NO 6
<211> LENGTH: 15
<212> TYPE: PRT
<213> ORGANISM: Artificial
<220> FEATURE:

```
<223> OTHER INFORMATION: Designed DNA sequence, does not originate
      from an organism

<400> SEQUENCE: 6

Gly Ala Thr Thr Cys Thr Cys Ala Ala Cys Thr Cys Gly Thr Ala
1               5                   10                  15

<210> SEQ ID NO 7
<211> LENGTH: 20
<212> TYPE: PRT
<213> ORGANISM: Artificial
<220> FEATURE:
<223> OTHER INFORMATION: Designed DNA sequence, does not originate
      from an organism

<400> SEQUENCE: 7

Ala Thr Thr Cys Ala Gly Ala Thr Thr Cys Thr Cys Ala Ala Cys Thr
1               5                   10                  15

Cys Gly Thr Ala
            20

<210> SEQ ID NO 8
<211> LENGTH: 44
<212> TYPE: DNA
<213> ORGANISM: Artificial
<220> FEATURE:
<223> OTHER INFORMATION: Designed DNA sequence, does not originate
      from an organism

<400> SEQUENCE: 8
atgactgtac gagttgagaa tctgaatcgg gcgcgaacgg gtat              44

<210> SEQ ID NO 9
<211> LENGTH: 16
<212> TYPE: PRT
<213> ORGANISM: Artificial
<220> FEATURE:
<223> OTHER INFORMATION: Designed DNA sequence, does not originate
      from an organism

<400> SEQUENCE: 9

Ala Thr Ala Cys Cys Gly Thr Thr Cys Gly Cys Gly Cys Cys Gly
1               5                   10                  15

<210> SEQ ID NO 10
<211> LENGTH: 51
<212> TYPE: PRT
<213> ORGANISM: Artificial
<220> FEATURE:
<223> OTHER INFORMATION: Peptide Sequence, not DNA

<400> SEQUENCE: 10

His Ile Ser His Ile Ser His Ile Ser His Ile Ser His Ile Ser His
1               5                   10                  15

Ile Ser Gly Leu Tyr Gly Leu Tyr Ser Glu Arg Gly Leu Tyr Gly Leu
            20                  25                  30

Tyr His Ile Ser His Ile Ser His Ile Ser His Ile Ser
        35                  40                  45

His Ile Ser
    50

<210> SEQ ID NO 11
<211> LENGTH: 45
<212> TYPE: DNA
<213> ORGANISM: Artificial
<220> FEATURE:
```

```
<223> OTHER INFORMATION: Designed DNA sequence, does not originate
      from an organism

<400> SEQUENCE: 11
actgactgta cgagttgaga atctgaatcg ggcgcgaacg ggtat            45

<210> SEQ ID NO 12
<211> LENGTH: 16
<212> TYPE: PRT
<213> ORGANISM: Artificial
<220> FEATURE:
<223> OTHER INFORMATION: Designed DNA sequence, does not originate
      from an organism

<400> SEQUENCE: 12

Ala Thr Ala Cys Cys Gly Thr Thr Cys Gly Cys Gly Cys Cys Gly
1               5                  10                  15
```

REAGENTLESS AND REUSABLE BIOSENSORS WITH TUNABLE DIFFERENTIAL BINDING AFFINITIES AND METHODS OF MAKING

CROSS REFERENCES TO RELATED APPLICATIONS

This application is a Division of application Ser. No. 11/094,540 filed on Mar. 25, 2005 now U.S. Pat. No. 7,435,386, the entirety of which is incorporated herein in full by reference. Ser. No. 11/094,540 is a Non-Prov of Prov (35 USC 119(e)) application 60/559,287 filed on Mar. 25, 2004, the entirety of which is incorporated herein in full by reference.

BACKGROUND OF THE INVENTION

Development of robust, sensitive, and reusable sensors is a strong current scientific priority. As such, recognition-based biosensors capable of specifically detecting chemicals, toxins, and bio-agents in their environment are of increasing importance. An important goal in biosensor evolution is production of nanoscale assemblies capable of continuously monitoring concentrations of target species in a simple, reliable manner. This is accomplished by designing sensor components to carry out analyte recognition and binding while simultaneously producing useful output signals via an integrated signal transduction system. Optically addressed biosensors of this type often employ fluorescence resonance energy transfer (FRET) in signal transduction.

FRET has been employed in carefully designed sensing systems for proteins, peptides, nucleic acids and other small molecules, see Medintz et al., *Nature Materials* 2003 2, 630. It is known in the art that other sensing modalities can be employed in the signal read-out of recognition-based biosensors, especially electrochemical modes or enzyme related systems, see Benson et al., *Science* 293, 1641-1644 (2001).

Biosensors function by reversibly linking bioreceptor-target analyte binding with closely integrated signal generation. Such sensors can either continuously monitor analyte concentrations or easily be returned to baseline read-out values by removal of analyte. Current bioassays on the market are single use or limited time use. Either they need to be replaced after each test or within a short time. This increases both test costs and the logistical demands for performing the analysis. Fielded biosensors can have complex robotics that handle the reagent storage and sensor surface replacement.

Sensor systems based on Surface Plasmon Resonance (SPR) can be regenerated, such as the Biacore SPR instrument. This sensor works by measuring the change in index of refraction at the sensor surface upon analyte binding. This works well for large molecules, but requires a harsh regeneration fluid that limits sensor lifetime. In addition, it works poorly in complex samples where nonspecific deposition to the surface interferes with the ability to discriminate actual signal.

Other systems can be used numerous times for the detection of small molecules, however as the fluorescent analog is displaced off the sensor surface the sensor is slowly consumed until it no longer functions. One example is the flow immunosensor of U.S. Pat. No. 5,183,740 to Ligler, et al.

Surface acoustic wave sensors with selective membranes exist for the sensitive detection of gas phase molecules. However, similar devices built for the liquid phase detection are less sensitive and have the same limitations as SPR.

FRET based assays have previously been described; however they are fluid phase methods that are effective for a single analysis only. This is also true for tests that depend on fluorescence anisotropy measurements, which are effective solution phase analyses but require the reagents to be freely moving to monitor a change upon binding.

A definition describing a biosensor has been proposed by IUPAC which provides that "a biosensor is a self-contained integrated device which is capable of providing specific quantitative or semi-quantitative analytical information using a biological recognition element (biochemical receptor) which is in direct spatial contact with a transducer element. A biosensor should be clearly distinguished from a bioanalytical system which requires additional processing steps, such as reagent addition. Furthermore, a biosensor should be distinguished from a bioprobe which is either disposable after one measurement, i.e. single use, or unable to continuously monitor the analyte concentration". Although biological recognition elements are employed in an extensive range of analytical formats, in few cases are they integrated into sensing devices and meet all these rigorous criteria.

The functional simplicity afforded by biosensors, allowing autonomous and continuous monitoring of chemical species, promises to make these devices useful in chemical process monitoring, pharmaceuticals screening, patient point-of-care and environmental testing, public health, and in defense-related fields.

Optically addressed molecular biosensors that meet the above criteria have been developed by Helling a et al., *Proc. Natl. Acad. Sci. USA* 1997, 94, 4366-4371, in which bacterial periplasmic binding proteins (bPBPs) were engineered to allow transduction of binding events to remote fluorescent signal-generating sites within the same protein by allosteric coupling. Recently, this strategy has been extended to allow surface tethering to unmodified hydrophobic surfaces of dye labeled-bPBPs by engineering of a self-adhering hydrophobic peptide onto the protein terminus, see Wada, et al, *J.A.C.S.* 2003, 52, 16228-16234.

FRET-based fusion protein biosensors that employ different colored green fluorescent protein (GFP) mutants linked to substrate binding domains that report binding events by coupled changes in conformation and energy transfer have also been developed, see Fehr, et al, *Proc. Natl. Acad. Sci. USA* 2002, 99, 98469851, and Fehr et al, *J. Biological Chem.* 2003, 278, 19127-19133. Both of these biosensor types are only useful for a small range of analysis targets. In the bPBP-based sensors, intramolecular transduction of binding events to integrated signaling centers requires highly specialized allosteric receptors. Even though computationally intensive redesign of the binding sites for recognition of alternate substrates may be feasible, binding pocket remodeling is unlikely to prove practical in providing sensors useful for monitoring a wide range of analytes. In sensors employing GFP fusion proteins, where differences in FRET efficiency between bound- and analyte-free receptor states result in signal generation, the range of bioreceptors that undergo obligatory ligand-dependent conformational changes is also very limited.

A variety of sensitive FRET-based single-measurement bioanalytical systems or bioprobes have been developed that detect peptides, proteins, and various small molecules in vivo and in vitro. See Scheller, et al, *Biotech.* 2001, 12, 35-40; Iqbal, et al, *Biosens. Bioelect.* 2000, 15, 549-578; O'Connell, et al, *Anal. Lett.* 2001, 34, 1063-1078; and Marvin, et al *Proc. Natl. Acad. Sci. USA* 1997, 94, 4366-4371. Maxwell, et al, *J. Am. Chem. Soc.* 2002, 124, 9606-9612, describes a gold nanoparticle-nucleic acid FRET biosensor that utilizes a probe DNA oligo in a 'molecular beacon' function to detect other DNA.

Biosensors that utilize FRET are also attractive due to the intrinsic sensitivity of FRET to small changes in donor-acceptor distance and orientation. Medintz, et al, *Bioconjugate Chem.* 2003, 14, 909-918 demonstrated the feasibility of using dye-labeled MBP and dye-labeled β-CD for FRET-based detection in solution. Rather than being a sensor, that homogenous system functions only in single-measurement bioanalysis.

BRIEF SUMMARY OF THE INVENTION

This invention provides a FRET-based surface-bound biosensor that overcomes the single-use limitation of previously known homogenous bioanalytical systems. The invention provides for fully reversible, reagentless, self-assembling biosensors. It is an object of the present invention to provide a biosensor design that can easily be adapted to target different analytes. It is another object of the invention to provide a biosensor that has a modular design for incorporating a wider range of available receptors as bio-recognition elements. It is a further object of the invention to provide a biosensor that uses multifunctional surface-tethered components. It is a further object of the invention to provide a biosensor that is regenerable or can operate in a continuous mode. These and other objects are provided by the invention disclosed below.

The biosensor of the present invention comprises a modular biorecognition element and a modular flexible arm element that reacts with the biorecognition element. The biorecognition element is tethered to a substrate and can be a protein, an aptamer, a carbohydrate, DNA or RNA molecule, among others. This biorecognition element is labeled with a fluorescent dye. The modular flexible arm is also tethered to a substrate, in an orientation that allows it to interact with the biorecognition element. The flexible arm contains an analog of the analyte that binds with the biorecognition element. Both elements are labeled with a fluorescent dye. When the elements bind, the dyes are brought in close proximity, which establishes a baseline fluorescence resonance energy transfer (FRET). When an analyte of interest is provided to the biosensor, the analyte will displace the analyte analog. The displacement of the analyte analog by the analyte will cause a change in the FRET signal in a concentration dependent manner. The sensor of this invention can be regenerated and returned to baseline levels by washing away analyte. A complex set of interactions exists on the sensing surface that contributes to overall sensor behavior and largely determines sensor dynamic range. This modular biosensor approach provides a way to assemble a wide range of useful biosensors that are regenerable, can be reused numerous times, or operated continuously and independently. Facile control of binding constants and sensing range is a built-in capability. The modularity of different portions of the biosensor allows functional flexibility. The biosensor is adaptable to measure many different analytes or targets. The biosensor operates without additional development reagents, requiring only the presence of analyte or target for function.

The recognition-based sensors of this invention are capable of specifically detecting chemicals, toxins, and bio-agents in their environment. These sensors employ a multifunctional molecular assembly in which a surface-immobilized biorecognition entity can reversibly bind to a surface-tethered entity immobilized on the same or suitably closely situated surface.

DETAILED DESCRIPTION OF THE INVENTION

Figure 1:
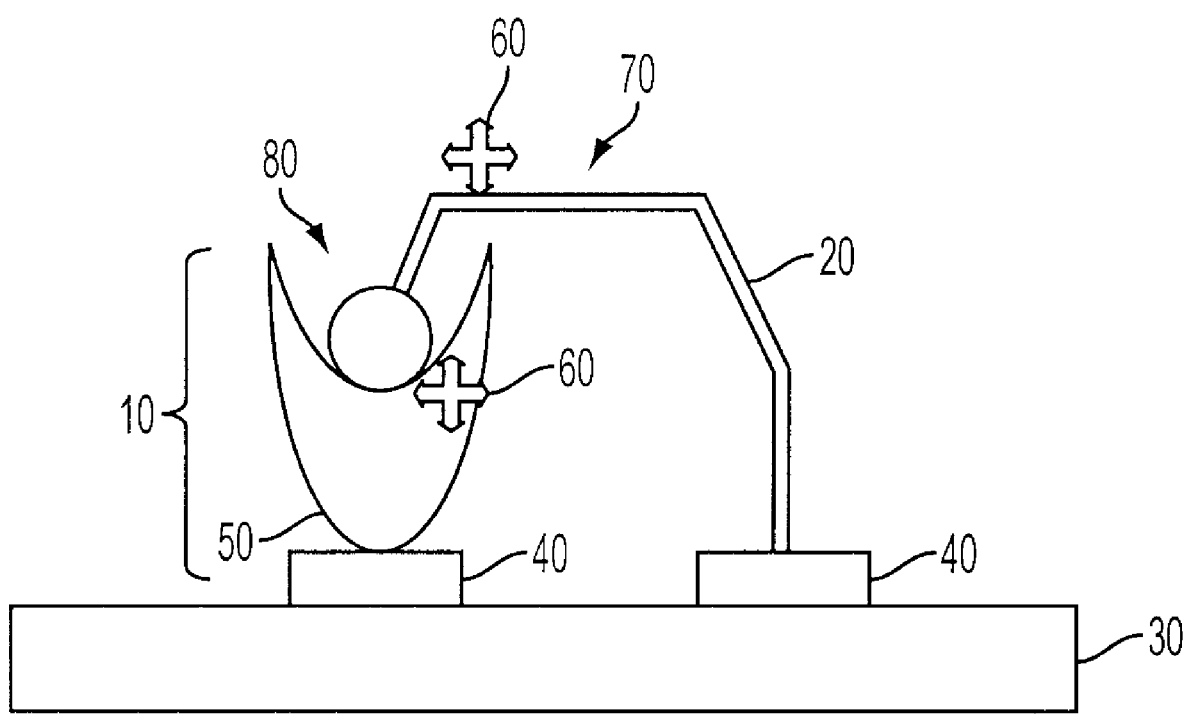
FIG. 1 depicts a schematic of the modular biosensor.
Figure 2:
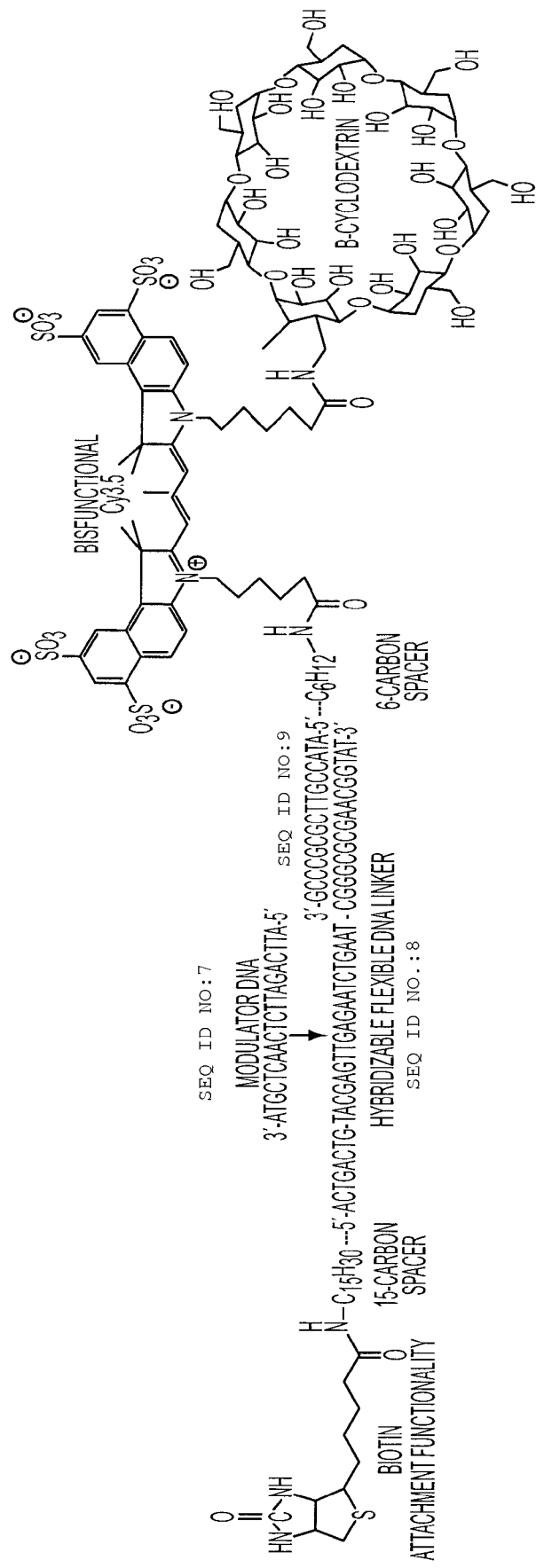
FIG. 2 depicts the structure of a modular arm of the MBP biosensor.

FIG. 1 depicts a schematic of a modular biosensor of the present invention. The biorecognition element (10) and the modular arm element (20) are tethered to a surface (30) by specific oriented surface attachment module (40). The surface attachment modules (40) includes, but are not limited to, biotin, avidin, antibody, reactive thiol, reactive amine, non-reversible enzyme substrate, protein A, protein G, protein L, DS-DNA, and PNA. Methods to accomplish surface attachment include, but are not limited to, biotin-avidin chemistry, metal-affinity coordination, thiol bonding, hydrophobic interactions, and DNA-directed immobilization. Other means known in the art can be utilized. The surface (30) can be a solid planar macromaterial or spherical or other shaped material, or a microscopic planar, spherical or other shaped micro- or nanomaterial, a nanocrystalline or modified nanocrystalline material, or a molecular or biomolecular assembly composed of protein, DNA, RNA, PNA, morpholino DNA, or other biomolecule and their derivatives, molecularly templated materials, naturally occurring polymers, minerals, and any similar base material. Those skilled in the art would understand that the biosensor of the present invention could be made without the use of a surface (30) by tethering the modular arm element (20) directly to the biorecognition element (10). The biorecognition element (10) allows for specific oriented surface attachment (40), and contains a biorecognition module (50) that is site specifically labeled with a signaling module (60). The types of biorecognition module (50) includes, but is not limited to, proteins, such as enzymes, receptors, bPBPs, antibody fragments, and peptides), aptamers, carbohydrates, DNA, PNA, and RNA. The modular arm (20) allows for specific oriented surface attachment (40), and comprises a flexible arm (70) and a recognition module (80), and has been site-specifically labeled with a signaling module (60). The flexible arm (70) is comprised of flexible moieties, including, but not limited to, SS-DNA, DS-DNA, combinations of SS-DNA and DS-DNA, thiolated DNA, RNA, thiolated RNA, linear homopolymers, linear copolymers, block copolymers, PNA, α peptides, β peptides, protein, polymer, or oligosaccharide. The signaling module (60) includes, but is not limited to, fluorescent dyes, quenchers, electrochemically active groups, quantum dots and enzymes. The recognition module (80) includes, but is not limited to, antigens, epitopes, analytes, substrates, proteins, peptides, toxins, sugars, biological agents, and analogs of said. The recognition module (80) is attached to the distal end of the flexible arm (70). The binding of the recognition module (80) with the biorecognition module (50) provides a biosensor that is in a ground state by bringing both signaling modules (60) into close proximity to each other. This close proximity establishes a baseline fluorescence resonancy energy transfer (FRET). Analyte added to the biosensor will competitively displace the recognition module (80). Signal transduction of the FRET is sensitive to the displacement of the recognition module (80). Binding affinity control can be achieved by, but is not limited to, stiffening of the flexible arm (70), using different affinity biorecognition elements, or by temperature.

It would be understood by those skilled in the art that the biosensor of this invention could be easily altered to detect a wide range of analytes of interest. Disclosed are the components and architecture of a biosensor as well as a method of preparing and assembling a reagentless and reusable biosensor with tunable differential analyte binding properties. This sensor consists of at least two macromolecular entities that are able to interact with each other for sensing. Both entities can be tethered to a surface.

Figure 4A:
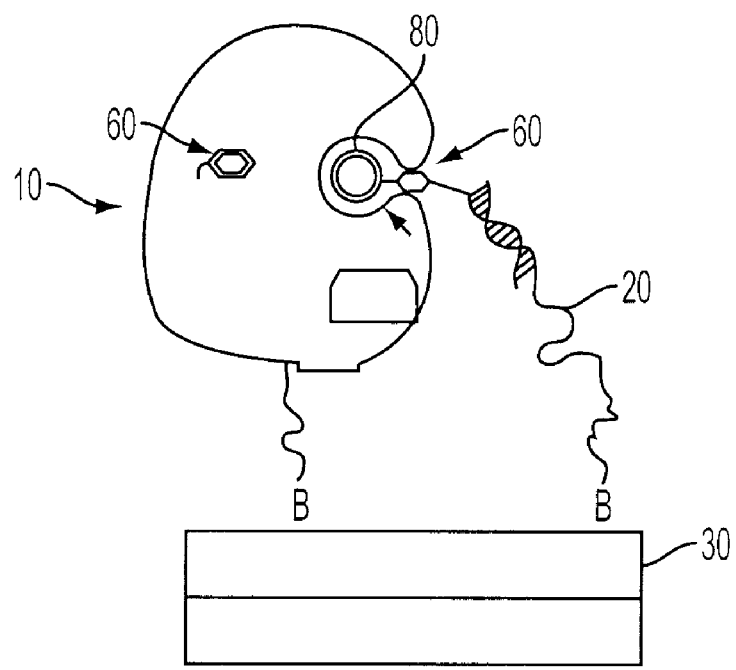
FIG. 4a shows a schematic of the MBP biosensor in its resting state

FIG. 4*a* depicts a schematic view of a biosensor for maltose in its resting state. The modular arm element (20) is bound to the biorecognition element, maltose binding protein (MBP), (10) by the recognition module (80), an analyte analog, β-cyclodextrin (β-CD), of the analyte of interest, maltose. The signaling elements (60) of the biorecognition element (10) and the modular arm element (20) are in close proximity, establishing a baseline FRET. It is understood by those skilled in the art that the close proximity for establishing FRET generally occurs in the range of about 1 to 10 nanometers.

Figure 4B:
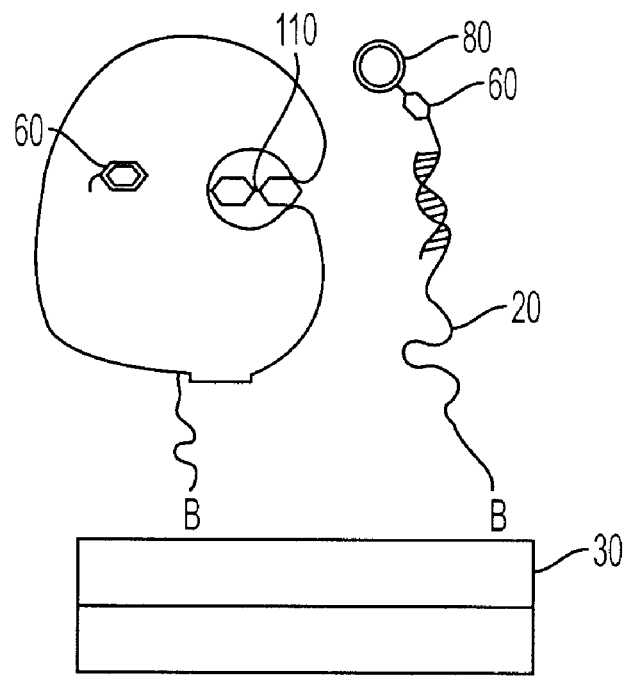
FIG. 4b shows a schematic of the MPB biosensor in the presence of an analyte

FIG. 4*b* depicts the schematic view of the biosensor after the introduction of analyte, maltose, (110) to the biosensor. The recognition element, β-CD, (80) has been displaced by the analyte (110), causing the flexible arm module (20) to move with respect to the biorecognition element. This causes the signaling element (60) of the biorecognition element, MPB, (10) and the signaling element (60) of the modular arm element to move with respect to each other, causing a measurable change in FRET. A detector would provide the means for providing the excitation light and detection means for measuring the FRET levels. The biosensor (100) can be washed to remove the analyte (110), regenerating the biosensor to the resting state of FIG. 4*a*.

Figure 5A:
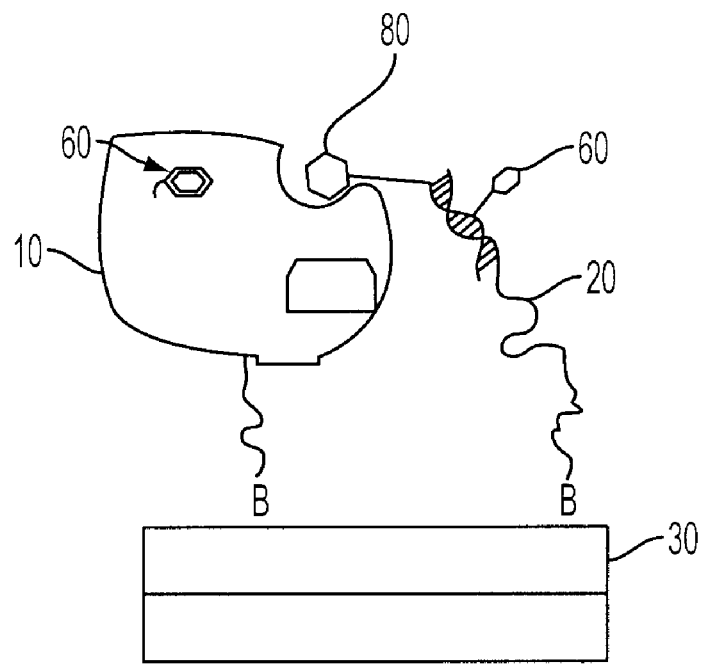
FIG. 5a shows a schematic of the TNT sensor in its resting state

FIG. 5*a* depicts the schematic view of the TNT biosensor in its resting state. The modular arm element (20) is bound to the biorecognition element, anti-TNT-scFv fragment (α-TNB), (10) by the recognition module (80), an analyte analog, (TNB), of the analyte of interest (110), TNT. The signaling elements (60) of the biorecognition element (10) and the modular arm element (20) are in close proximity, establishing a baseline FRET.

Figure 5B:
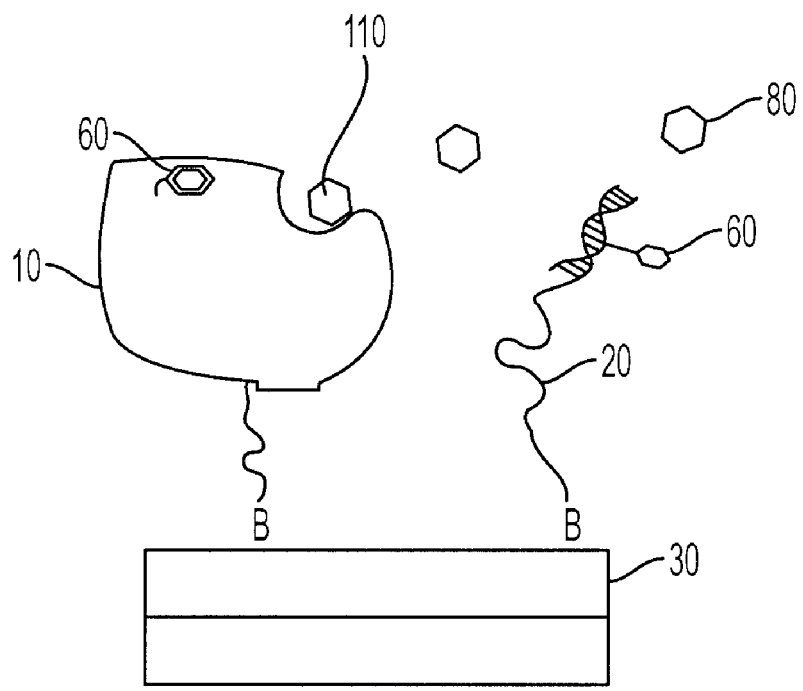
FIG. 5b shows a schematic of the TNT sensor in the presence of analyte
Figure 6:
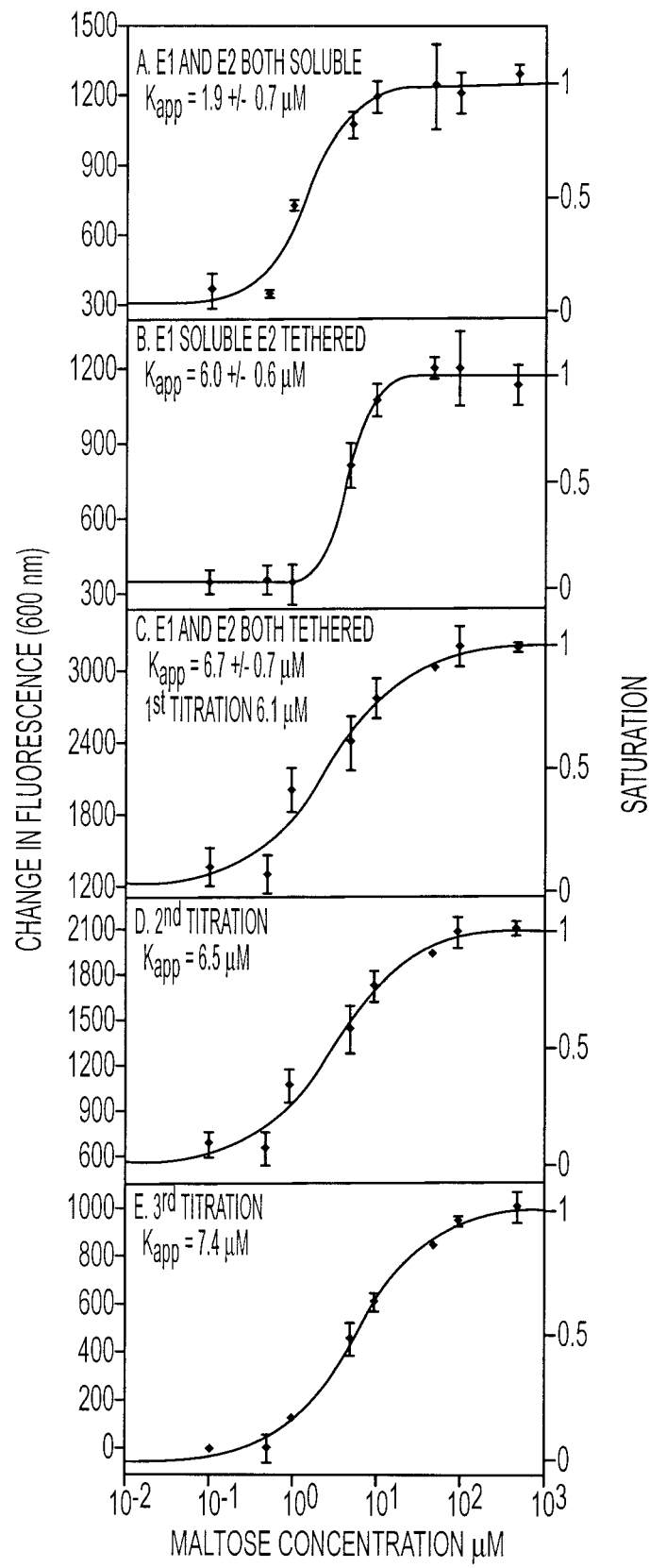
FIG. 6 is a series of graphs depicting the change in fluorescence in relation to analyte concentration.

FIG. 5*b* depicts the schematic view of the TNT sensor after the introduction of analyte, TNT (110) to the biosensor. The recognition element, α-TNB, (80) has been displaced by the analyte (110), causing the flexible arm module (20) to move with respect to the biorecognition element, α-TNB, (10). This causes the signaling element (60) of the biorecognition element, α-TNB, (10) and the signaling element (60) of the modular arm element to move with respect to each other, causing a measurable change in FRET. A detector would provide the means for providing the excitation light and detection means for measuring the FRET levels. The biosensor (100) can be washed to remove the analyte (110), regenerating the biosensor to the resting state of FIG. 4*a*.

Figure 7:
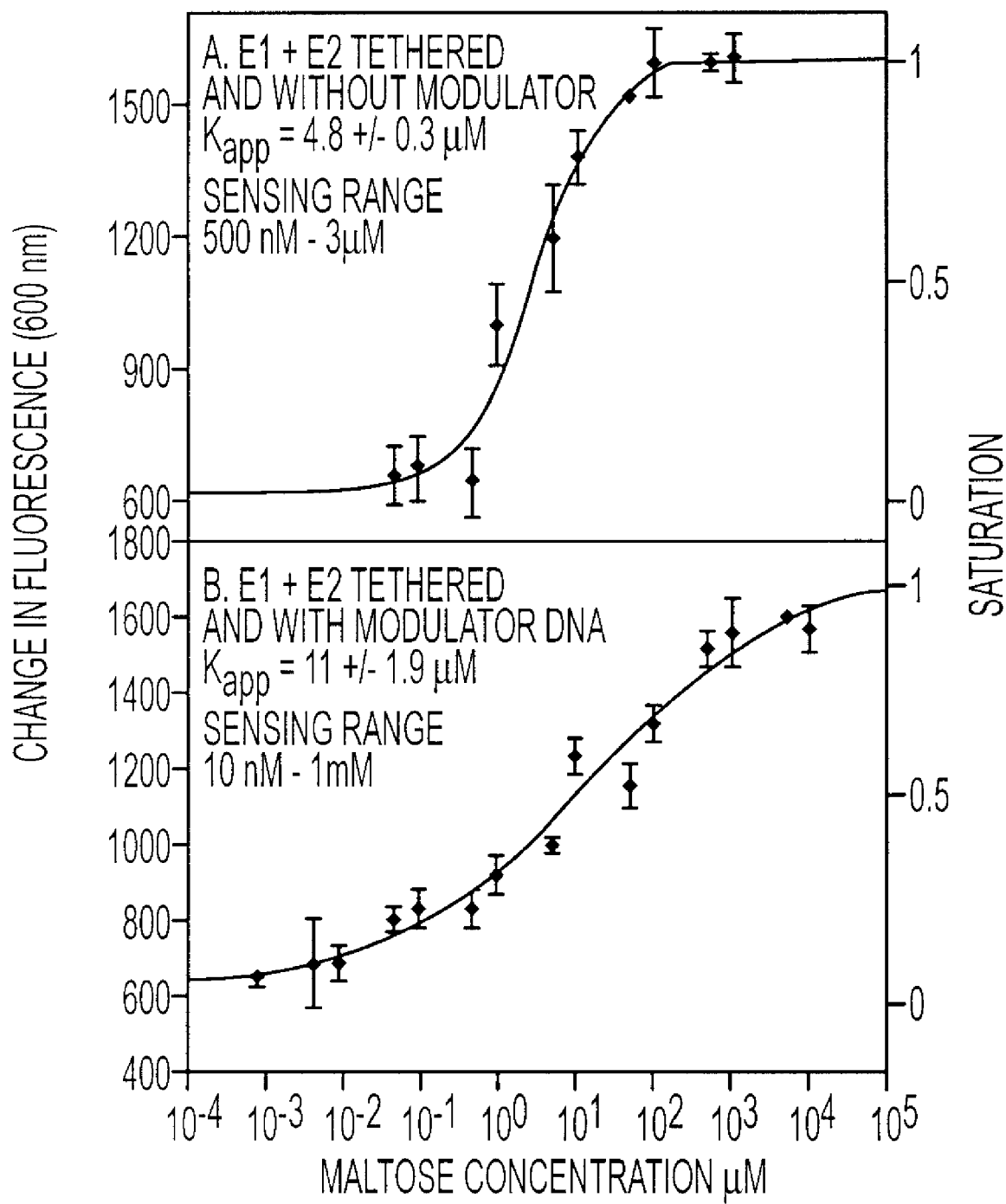
FIG. 7 is a graph depicting the change in fluorescence in relation to analyte concentration, demonstrating the effect of controlling binding properties when the flexible arm is stiffened with DNA.

FIG. 7 shows the effect of adding a modulator to the sensor that alters its binding characteristics. The sensor was self-assembled with Modular arm P1 tethered using oligo Bio3 and MBP95C QSY7 attached with Bio-X NTA. The resulting titration against maltose is show in the top graph A. A variant of the sensor described above with the addition of modulator DNA is depicted in bottom graph B. Useful sensing range is defined as the range from 10-90% fractional saturation.

In one embodiment of the invention, the biorecognition element consists of a specific protein, i.e. maltose binding protein (MBP) that has been dye-labeled. The modular arm element consists of an analyte analog (i.e. beta cyclodextrin), a signaling module (i.e. a cyanine dye), a flexible arm module (i.e. synthetic oligomeric DNA), and an immobilization module (i.e. biotin). The component modules of the modular arm element are chemically linked to each other in a linear fashion using synthetic chemical methods. In the sensor, the biorecognition module and the modular arm element recognize and bind with each other. Specifically, the protein saccharide binding site binds the cyclodextrin, and as the two incorporated dyes in the assembled sensor are in close proximity to each other, fluorescence resonance energy transfer (FRET) takes place and can be measured. Upon contact of the assembled sensor with target analyte, e.g. maltose or other structurally related sugar, displacement or replacement of the cyclodextrin from the dissacharide binding site of MBP occurs, causing the two incorporated dyes to move in space relative to one another, which results in a change in FRET that can be monitored.

Real or apparent binding constants or other relevant physical properties (linked to sensor sensitivity and/or dynamic range and/or chemical or thermal stability) of the biosensor can be altered by hybridizing DNA of different compositions and lengths to the flexible arm module, yielding control over sensing kinetics and thermodynamics. Additionally, variants of MBP with different intrinsic sugar binding properties can be substituted at will as the biorecognition element of the sensor, which also allows adjustment and control of sensor performance.

Because the biorecognition module and modular arm module are tethered to a surface, the target analyte can repeatedly be washed away and the sensor regenerated to a resting state ready for another sensing event. The sensor can also function as a completely independent, continuously functional monitor for an analyte in an environment where the concentration of the analyte can change over time, such as in a stream of flowing liquid, where a detector, i.e., a supply of exciting light and detector of optical signals are present. Furthermore, given the tethered design, protein receptors and analogs that may not normally bind together in solution can be forced to interact cooperatively for sensing events.

The sensing assembly is easily immobilized and assembled on microtiter well surfaces, takes advantage of biological specificity, links target binding with signal generation, and functions in a reversible and regenerable manner. Controlled immobilization and orientation of proteins while maintaining their relevant activity on a solid surface remains challenging. To accomplish this, previous biosensor assemblies have been described that rely on hydrogel encapsulation of sensor components. The method of the present invention uses an approach that relies on self-assembly of components upon a protein-passivated surface. The degree of structural and functional control afforded by this approach makes this general assembly method ideal for assembling a variety of receptors for sensing wide range of targets. Beginning with the concept of surface-tethering all sensor components, several key design features were considered. In order to immobilize and organize the required molecular elements, reliance on readily accessible and robust avidin-biotin assembly methodology was desirable, so the sensor was assembled on NA-coated microtiter plate wells and monitored with a fluorescent microtiter plate reader, technology readily accessible or already present in many biological testing laboratories.

Methods utilized for surface confinement of both bioreceptor and analyte analog, maltose binding protein and β-CD in this case, needed to provide sufficient freedom of motion for displacement of the analyte analog by the target analyte during sensor operation. To accomplish this, a multifunctional modular sensor arm was conceived that would be structurally flexible, yet incorporate the analyte analog, FRET donor dye, and surface-tethering element in a single chemically linked unit. A ternary B-CD-Cy3.5-DNA oligonucleotide tether arm that could be immobilized by DNA directed immobilization (DDI), but easily made using commercially obtained materials, was selected to fill this role. Complementary base pairing specificity in DDI allowed a high degree of spatial control in sensor self-assembly and placed the extended flexible tether arm onto the NA surface in an oriented fashion in close contact with the protein receptor. Similarly, oriented immobilization of His-tagged MBP bioreceptor variants was assured by using engineered versions of the protein that allowed single-point attachment to the NA surface via biotin-X-NTA. As oligohistidine sequences are incorporated into many cloned and expressed proteins for metal affinity purification, many types of bioreceptors should be able to function in similarly constructed sensors after being labeled with an appropriate site-specific quencher dye.

Means for potentially modulating sensor performance were also considered and incorporated in the system. Sensors can easily accommodate 'switching in' of mutant receptor proteins as well as changes in the length or composition of DNA tethering elements to effect alteration of sensor performance.

There are several useful features of the present sensor design. The sensor can function with either of the two FRET dyes acting as energy donor or acceptor. Although only two dye pairs were used in the current work, the numerous FRET dye pairs available can provide the basis for the construction of multiple sensor versions, including an array or 'multiplex' sensing surfaces or devices. The present prototype sensor could be regenerated and re-titrated with maltose several times, yielding essentially the same binding constant with each subsequent titration. In its present configuration, 8 to 10 uses were possible before useful changes in fluorescence were eliminated, perhaps due to cumulative FRET dye photobleaching, MBP denaturation, or gradual dissociation of sensor components from the polystyrene surface during washing. However, the fact that the sensor assembly could be regenerated, re-used and yield essentially the same result is very encouraging.

Sensors based on this invention can be preassembled, dried, shipped, and reconstituted for use in the field. One advantage is the relatively small loss sensor performance due to tethering of all components to a surface. The effective concentrations of the surfaced-confined elements, present in approximately equimolar amounts, are undoubtedly very large, yet relatively low maltose concentrations were able to activate the sensor. The significant broadening of the binding curve for maltose, relative to the binding curve obtained for the components free in solution, indicates that a heterogeneous set of interactions between sensor components takes place on the surface. A subset of surface components have relatively optimal binding interactions between tethered β-CD and MBP so that they respond only to high concentrations of maltose. This subset is useful for sensing soluble sugar at high concentration, but is unresponsive to maltose at lower concentrations. Another surface-bound component subset forms interactions that are much less optimal for binding of the pendant β-CD of the DNA-dye-cyclic polysaccharide tethered arm within the MBP sugar binding site. In this case, maltose competes effectively for binding when present at much lower concentrations. Paradoxically, rather than being a liability for sensing, the effect of this surface heterogeneity is to expand the effective dynamic range of the system. In fact, this unexpectedly complex behavior functions to ameliorate the limited dynamic range that is a fundamental problem in most recognition-based sensing systems. Furthermore, greater control of sensor dynamic range can be accomplished by formation of even more complex surfaces, such as demonstrated here by use of alternate DNA tether arms with hybridized modulator DNA.

Progressive changes of the shape of the analyte binding curve over a relatively small temperature range above ambient (25-40° C.), leading to an endpoint at the upper temperature where sensor response approaches ideal apparent two-state binding behavior suggests "melting away" of most or all of the low-energy surface interactions contributing to surface heterogeneity. Initial heterogeneity of the complex sensor surface leading to the observed behavior could result from a wide variety of molecular interactions. Inter- or intramolecular DNA, DNA-protein (with MBP and/or neutravidin), and/or interactions of any or all of the components with the substrate polystyrene surface could play a role. Most likely, a complex synergistic interplay among the sensor elements due to the above interactions leads to the observed behavior. Predictable control and optimization of sensor surface behavior is a goal for future efforts, in which additional systematic alterations of sensor component properties (such as very careful design of DNA components to eliminate possible low-melting intramolecular hairpin formation) needs to be carried out. Nonetheless, even in the absence of extensive optimization of the materials employed, the sensor surfaces we have constructed are able to function as sensors, and function repeatedly, which suggests that the overall assembly strategy employed is quite robust.

The modulation of sensor behavior achieved by changing the structure and composition of the synthetic DNA used in the modular tether arm demonstrates a way of fine tuning the sensors of the present. While recently reported work demonstrated irreversible off-to-on switching by annealing of complementary DNA to an engineered enzyme-containing assembly, the present sensor design is the first to make use of DNA-DNA interactions to modulate the binding properties of a fully reversible biosensor assembly. When DNA is used for tethering and modulation purposes in similar designs, secondary structure considerations must be carefully examined. Furthermore, although examples disclosed have used DNA for the tethering and modulation functions of the biosensor, a wide range of other materials are feasible for sensor arm construction, including PNAs, peptides, and other linear oligomeric or polymeric materials. Similarly, non-protein receptors such as DNA or RNA aptamers, templated surfaces, or other types of molecular receptors can function as recognition elements. Although quenching of organic dyes for biosensor signal generation was used in the examples herein, use of optical components such as quantum dot energy donors, or altogether different read-out modalities, such as enzymatic or electrochemical monitoring, are also possible.

The foregoing example exemplifies only one biosensor assembly that can be prepared using the architecture, components and methodology described in the invention. Using different components, but using the same or similar basic architecture and assembly methods, a very large number of sensors, each having the novel features described, may be prepared.

Having described the invention, the following example is given to illustrate specific applications of the invention, including the best mode now known to perform the invention. These specific examples are not intended to limit the scope of the invention described in this application.

EXAMPLE 1

Biosensor for Maltose

Maltose Binding Protein. In this assembly, the bio-recognition elements employed are engineered variants of *E. coli* maltose binding protein (MBP). MBP, a well-characterized member of the bPBP superfamily, has been used extensively for prototyping purposes in the previously described biosensors, as well as in redox- and quantum dot-based hybrid FRET biosensors. Binding of maltose to MBP is accompanied by a conformational change; however, the FRET-based biosensor does not depend on a change in conformation for signal generation.

As illustrated in FIG. 4*a*, Quencher-dye (60) labeled biotinylated *E. coli* maltose binding protein (MBP) (10) bound in a specific orientation to a NeutrAvidin-coated surface (30) is employed as a biorecognition element (10). To complete sensor formation, a flexible arm module (20) comprised of a flexible biotinylated DNA oligonucleotides (115), a fluorescence resonance energy transfer (FRET) donor dye (60), and a distal β-cyclodextrin (β-CD) analyte analog (80) is bound in an equimolar amount to the same surface by means of DNA directed immobilization. After self-assembly, a baseline level of FRET quenching is observed due to specific interaction between the β-CD of the flexible tether arm and the sugar binding site of MBP, which brings the 2 dyes into close proximity. Addition of the target analyte, maltose, displaces the linked β-CD-dye of the DNA-based tether arm, and a concentration dependent change in FRET results. Biosensor sensitivity and dynamic range can be controlled by either using MBP variants having different binding constants or by binding of modulator DNA oligonucleotides that are complementary to the flexible DNA tether The biosensor is self-assembled on a NeutrAvidin™ (NA)-coated surface, and the basic sensing unit consists of an MBP bio-recognition element that binds the cyclic sugar β-cyclodextrin (β-CD) that is co-immobilized on the same surface as part of a multifunctional modular "tether arm." The distal β-CD element of this modular tether arm is linked to an integrated dye molecule that functions in signal generation. The target analog and signal transduction functionalities (β-CD and dye) in the same module are anchored to the sensor surface by hybridized DNA interactions via DNA-directed immobilization (DDI) utilizing modified oligonucleotides. Following biosensor assembly, an appropriate sugar analyte (e.g. maltose) can compete with β-CD for binding at the MBP binding site. Movement of the β-CD analyte-analog into or out of the protein binding site is coupled with obligatory movement of the integrated signaling dye, and this spatial displacement forms the basis for quantitative reporting of analyte sugar concentration by changes in FRET. The present biosensor, which is composed of molecular components that exist in direct spatial contact, and that is functional in a quantitative, continuous, and reversible manner that requires no additional or secondary reagents meets the rigorous criteria that define a biosensor.

MBP95C, MBP80C and MBP-AT (containing the specific AviTag recognition sequence for in vivo biotinylation) were engineered and expressed as described below. The DNA coding sequence for MBP protein (Mr~44 kD) is contained on a standard multicopy plasmid vector containing the ampicillin resistance gene and was expressed. This MBP gene sequence was engineered to express a C-terminal 5 histidine sequence along with aspartate 95 or threonine 80 changed to cysteine (MBP95C, MBP80C) using standard gene assembly and cloning techniques. To create an MBP that expresses the AviTag specific biotinylation sequence, a MBP mutant plasmid was engineered with codons changed to those recognized by XhoI and HindIII 27-30 and 15-18 bps, respectively, from the C-terminal penta-histidine coding sequence. The plasmid was then digested with XhoI and HindIII and oligonucleotides for a modified AviTag sequence ligated into these sites which coded for the sequence: AGLGGLNDIFEAQKIE-WHE. In vivo, biotin is covalently attached to the lysine, K, residue in this sequence. Transformants were screened and sequenced for correct integration. This MBP-AT (AviTag) plasmid was co-transformed into *E. coli* strain AVB99 along with pACYC184 (Avidity, Denver Colo.), which expresses the biotin holoenzyme synthetase BirA. Cells were grown overnight in 100 ug/mL ampicillin/10 ug/mL chloramphenical media and induced with isopropyl β-D-1-thiogalactopyranoside (IPTG) and 50 μM d-biotin. MBP-AT was purified and biotinylated MBP-AT was further purified using the ImmunoPure Immobilized Monomeric Avidin Kit (Pierce, Rockford Ill.). The MBP sequence (SEQ ID NO:1) with locations of 80C and 95C highlighted is below. Position of codons changed to XhoI and HindIII also shown.

```
                                                    SEQ. ID NO: 1
Met Lys Thr Glu Glu Gly Lys Leu Val Ile Trp Ile Asn Gly Asp Lys

Gly Tyr Asn Gly Leu Ala Glu Val Gly Lys Lys Phe Glu Lys Asp Thr

Gly Ile Lys Val Thr Val Glu His Pro Asp Lys Leu Glu Glu Lys Phe

Pro Gln Val Ala Ala Thr Gly Asp Gly Pro Asp Ile Ile Phe Trp Ala

His Asp Arg Phe Gly Gly Tyr Ala Gln Ser Gly Leu Leu Ala Glu Ile

*80*
Thr Pro Asp Lys Ala Phe Gln Asp Lys Leu Tyr Pro Phe Thr Trp Asp

*95*
Ala Val Arg Tyr Asn Gly Lys Leu Ile Ala Tyr Pro Ile Ala Val Glu
```

-continued

```
Ala Leu Ser Leu Ile Tyr Asn Lys Asp Leu Leu Pro Asn Pro Pro Lys

Thr Trp Glu Glu Ile Pro Ala Leu Asp Lys Glu Leu Lys Ala Lys Gly

Lys Ser Ala Leu Met Phe Asn Leu Gln Glu Pro Tyr Phe Thr Trp Pro

Leu Ile Ala Ala Asp Gly Gly Tyr Ala Phe Lys Tyr Glu Asn Gly Lys

Tyr Asp Ile Lys Asp Val Gly Val Asp Asn Ala Gly Ala Lys Ala Gly

Leu Thr Phe Leu Val Asp Leu Ile Lys Asn Lys His Met Asn Ala Asp

Thr Asp Tyr Ser Ile Ala Glu Ala Ala Phe Asn Lys Gly Glu Thr Ala

Met Thr Ile Asn Gly Pro Trp Ala Trp Ser Asn Ile Asp Thr Ser Lys

Val Asn Tyr Gly Val Thr Val Leu Pro Thr Phe Lys Gly Gln Pro Ser

Lys Pro Phe Val Gly Val Leu Ser Ala Gly Ile Asn Ala Ala Ser Pro

Asn Lys Glu Leu Ala Lys Glu Phe Leu Glu Asn Tyr Leu Leu Thr Asp

Glu Gly Leu Glu Ala Val Asn Lys Asp Lys Pro Leu Gly Ala Val Ala

Leu Lys Ser Tyr Glu Glu Glu Leu Ala Lys Asp Pro Arg Ile Ala Ala

Thr Met Glu Asn Ala Gln Lys Gly Glu Ile Met Pro Asn Ile Pro Gln

Met Ser Ala Phe Trp Tyr Ala Val Arg Thr Ala Val Ile Asn Ala Ala

Ser Gly Arg Gln Thr Val Asp Glu Ala Leu Lys Asp Ala Gln Thr Lys Leu

/ XhoI /       / HindIII/
Thr Lys Gly Ser His His His His His
```

Mutant proteins were specifically labeled on cysteine residues using maleimide activated Cy3 dye (extinction coefficient 150,000 $M^{-1}cm$, quantum yield >0.15, Amersham Biosciences, Piscataway N.J.) or QSY 7 dye (extinction coefficient 90,000 $M^{-1}cm^{-1}$, Molecular Probes, Eugene Oreg.).

β-CD-Cy3.5-P1 DNA Synthesis and Mass Spectral Analysis: Bisfunctional NHS-ester activated Cy3.5 dye (extinction coefficient 150,000 $M^{-1}cm^{-1}$, quantum yield >0.15, Amersham Biosciences) solubilized in 0.136M Na tetraborate buffer pH 8.5 was added to a vial containing ~5 nanomoles amino-functionalized P1 DNA. After reacting for 20 min at room temperature in the dark, a 100-fold excess of monoamino-beta-cyclodextrin was added. After 4 hrs, 200 μL of HE buffer (10 mM HEPES, 1 mM EDTA, pH 7.0) was added and the product precipitated with 25 μL—3M NaCl and 650 uL cold ETOH at −20° C. The precipitate collected by centrifugation was washed 4 times with ETOH and dried in a vacuum centrifuge. Dried pellets were solubilized in HE buffer and synthetic products separated from underivatized dye on 12% acrylamide gels by electrophoresis. Product band(s) were excised and the β-CD-dye-DNA adduct (abbreviated as P1) eluted by passive diffusion into HE buffer. Adduct(s) were concentrated/desalted using an oligonucleotide purification cartridge, OPC. Pure products were subjected to mass spectral analysis. Samples were de-salted and removed from non-volatile buffer(s) by solid phase extraction using C18 zip tips. Samples were bound to the tip and washed 3× with high purity water, 0.1% trifluoroacetic acid (TFA). Samples were subsequently eluted with 10 μL of 75% acetonitrile (ACN), 0.1% TFA, added to 90 μL of MALDI matrix (35 mg/ml 3-hydroxypicolinic acid in 30% ACN, 10 uL of 50 mg/ml ammonium citrate). One μL of each solution was deposited onto the MALDI plate. Samples were analyzed by MALDI-TOF mass spectrometry using a Voyager-DE PRO. Using the negative ion and linear TOF modes, signal was detected for the ternary product consisting of cyclodextrin-Cy3.5 dye-P1 DNA at m/z 7068. The mass calculated for the cyclodextrin-Cy3.5 dye-P1 amine DNA complex (P1) was 7073 amu. The synthetic product consisting of P1 DNA-Cy3.5 dye (without appended β-CD) was similarly isolated and identified.

Sensor Assembly: Reacti-Bind Neutravidin (NA) Coated Plates or opaque white microtiter plates coated with NA were prepared. For each microtiter well, 7-10 picomoles of P1 (SEQ ID NO. 2) were allowed to hybridize to the same amount of complementary biotinylated attachment DNA (Bio1 (SEQ ID NO. 3), 2 (SEQ ID NO. 4), 3 (SEQ ID NO. 5)) in Tris-EDTA buffer pH 8 (TE). Modulator DNA Mod1 (SEQ ID NO. 6), Mod2 SEQ ID NO. 7) was added where indicated in 2-fold concentration. The DNA containing solutions were heated to 80° C. for 5 minutes and then cooled slowly to room temperature to preclude any possible secondary structure formation. This solution was then diluted into 50 μL PBS and added to each NA microtiter well for 1 hour of binding at RT. Wells were washed with 200 μL PBS and 10 picomoles of biotinylated-MBP-AT95C-Cy3 added to each well in 50 μL PBS where indicated. Alternatively, 50-80 picomoles of MBP95C-QSY7 or MBP80C-QSY7 was preincubated with an equimolar amount of biotin-X nitrilotriacetic acid tripotassium salt (Biotin-X NTA, Biotium, Hayward Calif.) for 2 hrs at room temperature and added in 50 μL PBS to wells containing P1. The final, mixed sensor was allowed to bind and self assemble for 1 hr at room temperature, washed with 200 μL PBS and equilibrated in 50 μL PBS for 15 min before addition of sugar for testing. Sensors were regenerated by washing with 20 volumes of buffer and allowing the sensor to re-equilibrate for 20 min to 1 hr in 50 μL PBS. The table below lists oligonucleotides sequences referenced. In the table, sequence P1 is SEQ ID NO:2, Sequence Bio1 is SEQ ID NO:3, Sequence Bio2 is SEQ ID NO:4, Sequence Bio3 is SEQ ID NO:5, Sequence Mod1 is SEQ ID NO:6, and Sequence Mod2 is SEQ ID NO:7.

| SEQ ID NO: | Name | # of nucleotides | Sequence 5'-3' | TM °C. |
|---|---|---|---|---|
| SEQ ID NO: 2 | P1 | 16 | NH2-$C_6$-ATACCGTTCGCGCCCG | 61.8 |
| SEQ ID NO: 3 | Bio1 | 24 | Bt-$C_{15}$-ACTGACTGCGGGCGCGAACGGTAT | 69.7 |
| SEQ ID NO: 4 | Bio2 | 34 | Bt-$C_{15}$-ACTGACTGGAATCTGAATCGGGCGCGAACGGTAT | 71.9 |
| SEQ ID NO: 5 | Bio3 | 44 | Bt-$C_{15}$-ACTGACTGTACGAGTTGAGAATCTGAATCGGGCGCGAACGGTAT | 74.0 |
| SEQ ID NO: 6 | Mod1 | 15 | GATTCTCAACTCGTA | 48.0 |
| SEQ ID NO: 7 | Mod2 | 20 | ATTCAGATTCTCAACTCGTA | 54.3 |

Fluorometry and Titration: Fluorometric analysis of microtiter well plates was performed on a Safire Dual Monochromator Multifunction Microtiter Plate Reader. For the Cy3-Cy3.5 fluorophores, samples were excited at 520 nm and emission collected at 605 nm. Excitation at 550 nm and 600 nm emission were used for the QSY 7-Cy3.5 pair. For titrations, 5 μL of each appropriate sugar solution was added and mixed at RT for 5 min as described. Background fluorescence was subtracted and data normalized for volumetric changes. Data was transformed using a Hill 4-parameter plot and approximate binding constants, $K_{app}$, estimated in these conditions of multiple equilibria along with useful sensing ranges using SigmaPlot. For all titrations, the Hill coefficient approached 1, indicating a 1:1 maltose/MBP interaction.

Sensor Self-Assembly and Testing: Organized self-assembly of both the dye-labeled MBP receptor and extended modular arm bearing the β-CD analyte analog and reporter dye occurs on NA coated microtiter plates. It is possible to assemble the sensor components either by mixing equimolar amounts of the dye-labeled biotin-functionalized MBP and β-CD-Cy3.5-P1DNA/Bio1, 2, 3 modular tether arm in solution before attachment to the NA surface or by allowing the separate components to bind separately and sequentially. If the separate components bind separately and sequentially, empirically determine the amount of first component bound to the surface to leave enough remaining accessible biotin-binding sites for filling in with the second sensor component.

The NA biotin binding sites on the surface are ~50% occupied by a biotin-X-NTA linker coordinated to MBP through a C-terminal pentahistidine extension. Depending on the sensor variation, the remainder of the biotin binding sites are occupied by single-stranded DNA oligomers of varying lengths (termed Bio1, Bio2, or Bio3 of 24, 34, 44 bases in length, respectively). Each surface-bound oligo being linked to the surface through a flexible 5' hydrophilic 15-atom biotinylated TEG (triethethyleneglycol) linker on one end and hybridized to β-CD-Cy3.5-P1DNA on the other. Thus, in the completely assembled sensor, the β-CD-FRET dye modules critical for sensing are held on the surface in close molecular proximity with bound MBP to form active sensing complexes.

On the fully assembled sensor surface, an equilibrium is established in which immobilized MBP is positioned to bind the pendant β-CD of the modular arm element within its sugar binding site. With this binding event, the FRET dye pair is simultaneously brought into position for a baseline level of fluorescence quenching to occur. Due to the relatively small size of the MBP molecule and favorable Förster R0 values for the dyes used, energy transfer between a fluorophore located at the binding site of MBP and a dye label placed virtually anywhere on the protein is highly efficient.

Native MBP binds both the disaccharide maltose (KD of 0.9 μM), and β-CD (KD of 1.8 μM) with similar affinities. In the biosensor, signal generation is designed to occur when added maltose competitively displaces β-CD from the MBP sugar binding site. An increasing degree of occupancy of the binding site by an increasing concentration of maltose, concomitant with decreasing binding site occupancy of the tethered β-CD, is coupled quantitatively with changes in FRET occurring between incorporated system dyes, forming the basis for sensor function. The sensor assembly is designed to be re-set to a baseline quenching state by simply removing maltose by washing/dilution, so that quantitative sensing can be carried out repeatedly. Alternatively, when assembled in a properly configured flow cell or fixed within a bioreactor, a derivative of this molecular sensor assembly may be able to continuously and reversibly monitor fluctuations in maltose concentration.

Below is the structure of the three part tetherable modular arm and the relevant absorption.

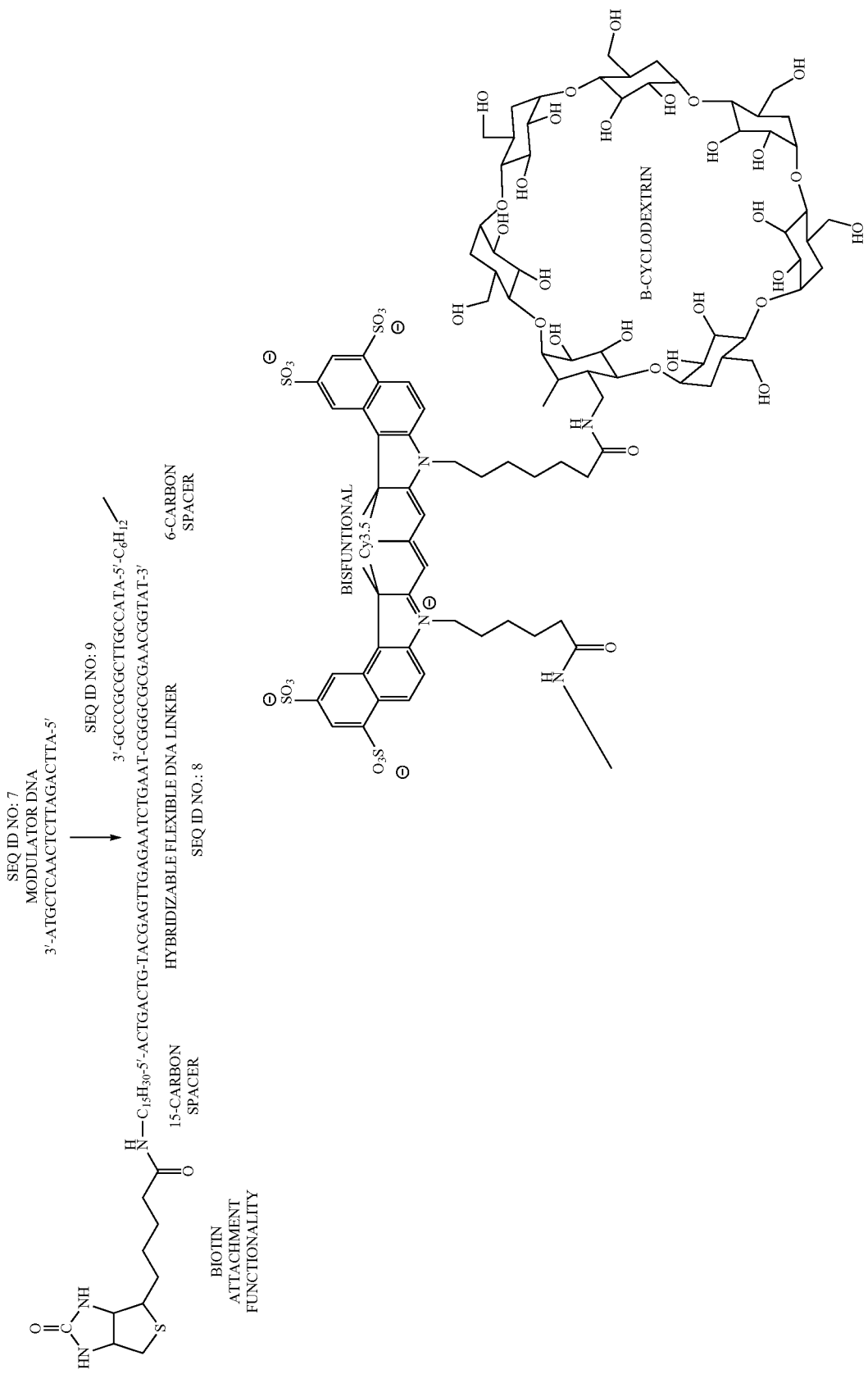

In this configuration, MBP was labeled at either of two engineered residues (80C or 95C) by thiol-reactive QSY 7, a dark (non-emitting) quencher dye. β-CD-Cy3.5-P1 (SEQ ID NO: 2) DNA was bound to the surface via the 34 nucleotide Bio2 (SEQ ID NO: 4) oligo and MBP95C-QSY7 was surface localized via biotin-X-NTA. In the initial state of the sensor (no maltose), proximity of the Cy3.5 donor dye of the tethered arm to MBP-bound QSY 7 acceptor dye resulted in partial quenching of Cy3.5 fluorescence. Emission of the Cy3.5 increased upon addition of maltose, strongly suggesting that competition for the MBP sugar binding site occurs between the soluble disaccharide and the β-CD moiety of the β-CD-Cy3.5-P1DNA modular arm. A change in average FRET quenching efficiency occurred due to a net difference in dye-dye distance/orientation in the system. The binding curve obtained was a smooth function of maltose concentration, but was relatively broad in the concentration dimension compared with titrations using soluble components (see below) suggesting that physical constraints related to tethering lead to inhomogeneity in the binding and signal generating apparatus. Nonetheless, the assembly performed effectively in sensing maltose.

After saturation with maltose, the sugar could be removed and the sensor reset to its baseline quenching value by rinsing the surface with buffer. Titration could then be carried out with essentially identical results, followed by repeated rounds of regeneration and sensing. The $K_{app}$ derived for maltose binding to this sensor was 6.7±0.7 µM. Control experiments were performed in which the β-CD-Cy3.5-DNA modular sensing arm was replaced with a partial sensing arm consisting of Cy3.5-P1DNA without the β-CD target analog recognition element. Titration of this control sensor assembly with maltose gave essentially no change in emission spectra or fluorescence intensity, demonstrating that function of the sensor depended on recognition of the β-CD moiety by MBP. Replacement of MBP with a non-functional protein (apomyoglobin bearing a C-terminal hexahistine) also resulted in no change in baseline emission with added maltose. The fluorescence does drop with regeneration, suggesting an upper limit to the number of regenerations even though essentially the same binding constant is derived with subsequent titrations.

Fluorescence changes during titration with maltose were also monitored with the same components present both in solution phase and in a "half-tethered" configuration. Starting with an equilibrium-state solution of 500 nM MBP95C QSY7 and 50 nM β-CD-Cy3.5-P1DNA, systematic changes in quenching that occurred due to competitive displacement of β-CD by maltose yielded a $K_{app}$ of 1.9±0.7 µM. Under these relatively dilute conditions, chosen to avoid inner filter effects, the β-CD containing reagent would be expected to occupy about 5-10% of the available binding sites of the MBP95C QSY7 present at equilibrium. The ~5% fluorescence change that occurred at maltose saturation was consistent with essentially complete displacement of the β-CD-Cy3.5-P1DNA. The binding curve for the soluble system was more compressed on the concentration axis compared to the binding curve of the fully tethered sensor, reflecting more ideal titration behavior for components freely diffusing in solution, and the $K_{app}$ value obtained from the binding data are consistent with previous MBP solution phase titrations.

In another titration, MBP95C QSY7 was present in solution at 40 nM, while β-CD-Cy3.5-P1DNA was tethered to the NA surface via DDI with biotinylated oligonucleotide Bio2. A $K_{app}$ for maltose binding of 6.0±0.6 µM was determined and the shape of the binding curve indicated retention of the essentially ideal binding behavior observed for the fully soluble system; thus, the cyclic sugar of surface-tethered β-CD-Cy3.5-P1DNA appeared to be presented to the soluble protein receptor in an essentially homogenous manner, unlike the fully tethered sensor assembly where geometric constraints leading to surface inhomogeneity are likely responsible for the broadened binding curve observed.

The behavior of the biosensor has only minimal dependence on the length of this tethering segment over the ranges investigated. Immobilization segments Bio1, Bio2, or Bio3 DNA of 24, 34, or 44 bases in length, respectively, were tested. The table below illustrates the sensor properties.

| Sensor Protein[1] | Functional Arm | Arm Attachment | Modulator | $K_{app}$ µM | Estimated useful sensing range[2] | % Fl increase upon sensor saturation[3] | Comment |
|---|---|---|---|---|---|---|---|
| MBP95C | P1 | NA | NA | 1.9 ± 0.7 | 350 nM-6 µM | 5 | Both components in solution |
| MBP95C | P1 | Bio2 | NA | 6.0 ± 0.6 | 2.5 µM-10 µM | 6 | Only P1 tethered via Bio2 |
| MBP95C | P1 | Bio2 | NA | 6.7 ± 0.7 | 1 µM-50 µM | 10 | P1 tethered via Bio2 & MBP95C tethered via Bio-X NTA |
| MBP95C | P1 | Bio3 | 1 | 4.0 ± 0.6 | 50 nM-650 µM | 7 | Modulator present |
| MBP95C | P1 | Bio3 | 2 | 11.3 ± 1.9 | 10 nM-1 mM | 9 | Modulator present |
| MBP95C | P1 | Bio1 | NA | 3.0 ± 0.3 | 1 µM-90 µM | 10 | |
| MBP95C | P1 | Bio3 | NA | 4.8 ± 0.3 | 500 nM-30 µM | 12 | |
| MBP80C | P1 | Bio3 | NA | 575 ± 15 | 10 µM-5 mM | 133 | |
| MBP80C | P1 | Bio3 | 2 | 404 ± 10 | 7 µM-5 mM | 127 | Modulator present |
| MBP80C | P1 | Bio3 | 2 | 375 ± 25 | 3 µM-3 mM | 36 | [4]See below |
| MBP95C/MBP80C | P1 | Bio3 | NA | 153 ± 27 | 4 µM-8 mM | 86 | Composite sensor |
| MBP-AT95C | P1 | Bio3 | NA | 10.5 ± 1.4 | 1 µM-150 µM | 6 | Biotinylated MBP-AviTag |
| MBP-AT95C | P1 | Bio3 | 2 | 9.3 ± 1.3 | 500 nM-100 µM | 5 | Biotinylated MBP-AviTag |

NA—Not applicable. AT—AviTag. All readings are performed at 20-22° C. See Suppl. for oligonucleotide sequences and FIG. 1 for schematic

[1]Unless otherwise noted, the protein is tethered to the neutravidin surface via the 5-histidine sequence using Ni-X NTA as in Methods
[2]This is the estimated concentration range for which these sensors can be used usefully and is defined as the range between 10% and 90% saturation.[ref 15,17]
[3]Calculated as $(Fl_{sat} - Fl_0)/Fl_0 \times 100$ where $Fl_{sat}$ = fluorescence at saturation and $Fl_0$ = fluorescence before the addition of sugar
[4]Plate with sensors in wells titrated 4 times consecutively, air dried and stored for 2 weeks in refrigerator and then titrated 3 times consecutively Using an estimated value of 3.4 Å for each base in a fully extended ssDNA linker, these linkers varied from ~82 to ~150 Å in potential length of the single-stranded segment. Binding constants obtained for these sensor variations remained in the low micromolar range, varying no more than ~2-fold, 6.7±0.7 µM for Bio2 versus 3.0±0.3 µM for Bio1. The behavior of the system assembled with Bio3, the longest tethering element, was similar to that for Bio1. The shape of the binding curve was similar in each case, and the net change in fluorescence between maltose-free and maltose-saturated states for each of the three variations tested was ~10%, demonstrating that the degree of functional surface coverage was not dependent on the ssDNA tether length. The behavior of the biosensor has only minimal dependence on the length of this tethering segment over the ranges investigated.

Modulation of Binding Affinity and Useful Sensing Range Effective means to modulate the sensitivity and/or dynamic range of the biosensor were sought. The first way explored for controlling sensor behavior involved relatively straightforward substitution of an MBP variant with altered sugar binding properties. A second variation on this form of control involved formation of a "mixed" composite sensor consisting of two sugar receptor variants on the same surface having different maltose binding profiles. A third level of sensor control involved hybridization of "modulator" DNA strands to the residual single-stranded section of the β-CD-Cy3.5-P1DNA/Bio3 tether arm in an attempt to alter the extension or stiffness of the tether arm by altering the ratio of ss/ds DNA in this modular component.

Figure 8:
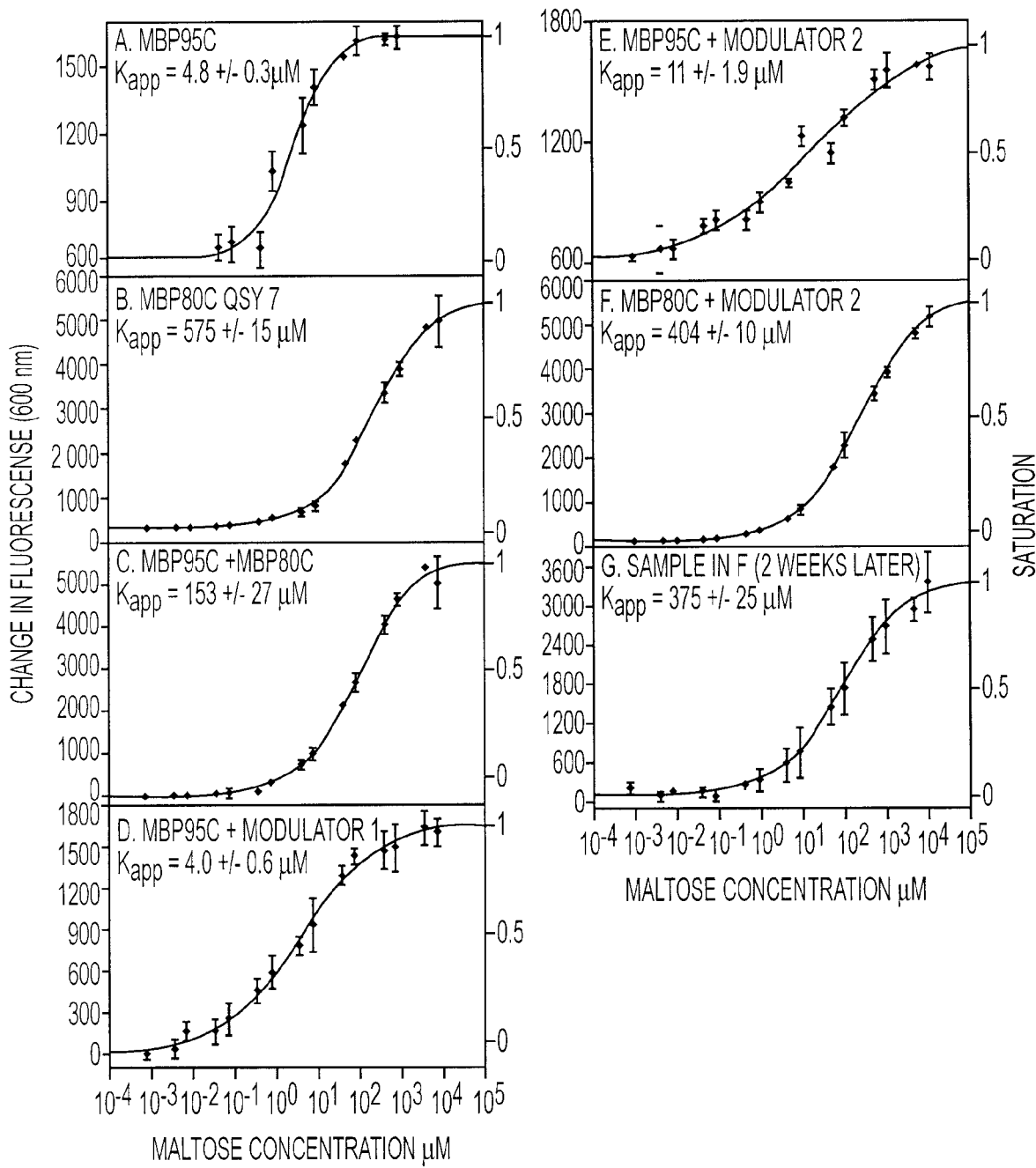
FIG. 8 is a series of graphs depicting the change in fluorescents in relation to analyte concentration.

As a first level of control, QSY 7-labeled MBP variant MBP80C having significantly different maltose binding characteristics from QSY 7-labeled MBP95C was used as the bioreceptor in order to modulate sensitivity and dynamic range. In this MBP variant, labeling at engineered cysteine-80 with the reporter dye significantly increases its $K_{app}$. Solution phase titration of Cy3-labeled MBP80C under similar conditions yielded a maltose KD of 70 µM. FIG. 8, in the graph labeled A, shows the binding curve from maltose titration of a sensor consisting of the β-CD-Cy3.5-P1DNA modular arm tethered with Bio3 and assembled with MBP95C QSY7, while FIG. 8, in the graph labeled B, shows data for the sensor constructed with MBP80C QSY7. The $K_{app}$'s and useful sensing ranges for the different sensor configurations are 4.8±0.03 µM/500 nM –30 µM and 575±15 µM/10 µM –5 mM, where useful sensing range was estimated from 10 and 90% sensor response to maltose. From these results it was clear that facile tuning of sensor sensitivity and dynamic range can be accomplished by altering receptor affinity. Combining receptor variants which have differing binding properties into a composite biosensor is one approach to creating biosensors with changed dynamic ranges. FIG. 8, in the graph labeled C, presents the results from maltose titration of a composite sensor assembled with equimolar proportions of MBP95C QSY 7 and MBP80C QSY7 receptors on the surface. Using this sensor assembly, there was a significant shift in $K_{app}$ (153±27 µM) and useful sensing range of ~4 µM-8 mM vs. 4.8±0.3 µM and 575±15 µM for the MBP95C QSY 7 and MBP80C QSY7 sensors, respectively. Not surprisingly, because of the significantly different intrinsic ΔF values for the two base sensor configurations, composite sensor properties were largely dominated by MBP80C QSY7 binding and signaling. By more closely matching net ΔF values of the constituent receptor components or adjusting ratios of each constituent sensor in the composite, finer control of sensor function could likely be achieved. Combinatorial screening methods could also be effective in optimizing composite sensors.

A third means to control sensor performance is modification of sensor properties by altering the extension or stiffness of the tether arm by changing the ratio of ss/ds DNA in β-CD-Cy3.5-P1DNA modular component was explored. Hybridizing complementary DNA to the tether arm will change a significant portion of the DNA in the tether arm from single-stranded (ss) to a more rigid double-stranded (ds) DNA form, and the resultant changes in rigidity of the DNA linker arm might allow control of sensor performance. The β-CD-Cy3.5-P1DNA/Bio3/Modulator DNA tether arm was self-assembled using DNA annealing by slow-cooling the combined heat denatured components (Temperature for all dsDNA-hybrids in the sensor was designed to be >65° C.) prior to room temperature immobilization on the NA surface along with MBP95C QSY 7. In the "unmodulated" β-CD-Cy3.5-P1DNA/Bio3 arm, only 16 of the available 44 bases in the Bio3 oligonucleotide (~35%) were involved in DNA duplex interactions. Hybridizing complementary MOD1 or MOD2 DNA to Bio3 in the β-CD-Cy3.5-P1DNA/Bio3 complex raises this number to 31/44 bases (~70%) or 36/44 bases (~82%), respectively. FIG. 8, in the graphs labeled D and E, show binding curves obtained from maltose titration of the MBP95C QSY 7 sensor with MOD1 or MOD2 oligonucleotides hybridized to their complements within the β-CD-Cy3.5-P1DNA/Bio3 modular assembly. The shapes of the binding curves for the modulated assemblies differ considerably from the binding curve of the unmodulated sensor, and different $K_{app}$ values and useful sensing ranges for the modulated assemblies are observed. Specifically, the binding curves for the oligonucleotide modified sensors are broader and shallower than that of the parent sensor, and the useful sensing ranges are correspondingly greater, ranging from 500 nM-30 µM for the unmodified sensor to 50 nM-650 µM for MOD1 and 10 nM-1 mM for MOD2 containing MBP95C QSY 7 sensors. Similar experiments utilizing MBP80C QSY7 resulted in small changes in $K_{app}$, but in this case the presence of modulator DNA did not significantly alter the useful sensing range. Changes in the packing of surface components due to the presence of modulator DNA could alter the binding behavior of MBP. Additionally, MBP is known to be very sensitive to small structural changes even distal from the binding site, which can significantly alter affinity. Clearly, this means of fine-tuning sensor properties can be successfully implemented, but at present the more direct methods previously described are more predictable and robust ways to modulate sensor function.

Stability of the immobilized sensor assemblies. Sensors assembled using MBP80C QSY7 and β-CD-Cy3.5-P1DNA/Bio3/MOD2 components were titrated with maltose in microtiter plate wells, purged of maltose by washing/dilution, then dried and stored at 4° C. for 2 weeks to determine long term stability and regenerability of the sensors. Following rehydration with PBS, successful maltose titration was carried out three times with regeneration. The $K_{app}$ of 375±25 µM obtained from the sensor attached to the dry-stored plate was identical, within error, to that of the initially tested sensor.

Sensor System Bioenergetics and Specificity. Maltose titration behavior was examined over a range of temperatures. Increasing concentrations of maltose were added to wells of a microtiter plate containing identical sensor assemblies based on MBP80C QSY 7 and β-CD-Cy3.5-P1DNA/Bio3. After equilibrating and reading the plate at 25° C., the plate was re-equilibrated at 30° C. and the fluorescence read with the same at 35 and 40° C. Of particular interest was the systematic change in the shape of the binding curve with temperature, from a broader binding isotherm at 25° C. to a more steeply rising curve at 40° C., suggesting that with increasing temperature the range of functional configurations of the tethered components becomes smaller, resulting in more ideal binding behavior at higher temperature. Sensor function is thus significantly temperature dependent. However, the temperature dependence of the shape of the binding curves makes it impossible to derive meaningful thermodynamic parameters in this complex system of multiple equilibria (e.g. Vant Hoff plots are likely to lack quantitative meaning). It is likely that sensor binding thermodynamics and kinetics would be affected by changes in other physical parameters such as pH, ionic strength and viscosity.

The ability of these surface-tethered maltose sensors to discriminate among different types of sugars was investigated by carrying out titrations with a range of sugars, including D-arabinose, D-galactose, D-glucose, lactose (an epimer of maltose), sucrose and β-CD, with maltose serving as the comparative standard. The table below

EXAMPLE 2

TNT Biosensor

The self-assembled modular sensing strategy can be applied to the detection of an analyte completely unrelated to maltose, namely, 2,4,6-trinitrotoluene (TNT), by altering two modules of the sensor assembly. Using the same sensor platform, a dye-labeled anti-TNT single-chain Fv antibody frag-

| Sugar | D-Arabinose | β-Cyclodextrin | D-Galactose | D-Glucose | Lactose | Maltose | Sucrose | H2O |
|---|---|---|---|---|---|---|---|---|
| | | P1-Bio3-MBP95C-QSY7-Bio-X NTA | | | | | | |
| Type[1] | Mono | Oligo (7-monomers) | Mono | Mono | Di | Di | Di | NA |
| Oligosaccharide Linkage | NA | α-1,4 glucosidic | NA | NA | 1,4-α glucosidic | α-1,4 glucosidic | α-1, β-2 glucosidic | NA |
| Δ FL[2] 100 nM | <1% | 14% | <1% | <1% | <1% | 100% | <1% | <1% |
| Δ FL[2] 1 mM | <1% | 58% | <1% | <1% | <1% | 100% | <1% | <1% |
| | | P1-Bio3-MOD2-MBP95C-QSY7-Bio-X NTA | | | | | | |
| Type[1] | Mono | Oligo (7-monomers) | Mono | Mono | Di | Di | Di | NA |
| Oligosaccharide Linkage | NA | α-1,4 glucosidic | NA | NA | 1,4-α glucosidic | α-1,4 glucosidic | α-1, β-2 glucosidic | NA |
| Δ FL[2] 100 nM | <1% | 28% | <1% | <1% | <1% | 60% | <1% | <1% |
| Δ FL[2] 1 mM | <1% | 73% | <1% | <1% | <1% | 100% | <1% | <1% |

[1]Mono, Di and Oligo - saccharide
[2]Δ FL = Percentage increase in PL intensity with respect to the initial value of the nanosensor, upon addition of the indicated amount of sugar, the response to 1 mM maltose defines the 100% comparison response
NA—Not applicable With sensors composed of either β-CD-Cy3.5-P1DNA/ Bio3 or β-CD-Cy3.5-P1DNA/Bio3/MOD2 and MBP95C-QSY 7, the only non-zero response obtained, excepting maltose was for β-CD. The binding specificity of MBP is fully retained on the sensor surfaces prepared.

Biotinylated MBP-AviTag Sensor Variant: Oriented attachment of the dye-labeled MBP to the NA surface for sensor construction has been accomplished in two different ways. The first method uses the heterobifunctional crosslinker Bio-X-NTA (where Bio is biotin, X represents an amino-methoxy spacer, and NTA stands for the nitrilotriacetic acid chelator functionality) to link C-terminally His-tagged MPB variants to the surface NA. Another MBP variation, MBPAT-95C, was also employed in sensor assembly. In this protein, an AviTag biotinylation recognition peptide was genetically fused to the C-terminus of the MBP sequence. The AviTag sequence allows specific in vivo biotinylation by the biotin holoenzyme synthetase BirA and subsequent isolation of site-specifically biotinylated proteins directly from E. coli lysates. MBPAT-95C was created to investigate whether MBP biotinylated in vivo could be used for attachment to the NA surface, thus eliminating the need for use of Bio-X-NTA or other potentially non-specific chemical biotinylation steps. Cy3-labeled MBPAT-95C was used to construct and test a Cy3-Cy3.5 emissive variant, where the Cy3.5 dye of β-CD-Cy3.5-P1DNA acts as an emissive FRET acceptor. The $K_{app}$ for maltose binding of 10.5±1.4 was similar to the value derived from MBP immobilized using Bio-X-NTA. Cy3-labeled MBPAT-95C functions well as the receptor, even though it is tethered to the surface by the biotinylated lysine of the 19-residue C-terminal AviTag peptide. Use of modulator DNA did not significantly alter sensor function. In vivo biotinylation of receptors thus represents another facile means to create components for use in sensor self-assembly. Successful use of this alternate receptor immobilization method implies that flexibility exists in the assembly strategy described herein.

ment (R-TNTscFv) was substituted for the MBP bioreceptor portion of the sensor and the multifunctional tether arm was modified to contain a dye attached to a modified internal base. The DNA arm is further modified to terminate with the TNT analogue 1,3,5-trinitrobenzene (TNB). FIGS. 5a and 5b schematically depict the TNT sensor. The R-TNTscFv portion is allowed to bind the TNB analogue, bringing both dyes into proximity, establishing a baseline level of FRET, and this complex is then self-assembled on a NA surface. Addition of TNT to the sensor solution results in a concentration-dependent change in FRET. In this configuration, the sensor retains its analyte specificity yet can still have its dynamic sensing range usefully adjusted. The sensor can be washed free of analyte and reforms for subsequent detection events. The demonstration that this sensor can be readily adapted to a completely different analyte highlights the utility of its modular construction and its general applicability to a variety of targets.

Explosive standards including TNT, TNB, hexa-hydro-1, 3,5-trinitro-1,3,5-triazine (RDX), 2-amino-4,6-dinitrotoluene (2A-4,6-DNT), and 2,4-dinitrotoluene (2,4-DNT) were obtained from Cerilliant Corp. (Austin, Tex.). Reactibind Neutravidin-coated plates were obtained from Pierce (Rockford, Ill.).

Mutagenesis and Protein Expression. The R-TNTscFv fragment, a derivative of TNB2 described in Goldman, et al, Journal of Env. Monitor; 2003, 5, 380-3, was engineered to express a HISHISHISHISHISHISGLYGLYSERG-LYGLYHISHISHISHISHISHIS (SEQ ID NO:10) carboxy terminus, where $(His)_6$=6-histidine residue sequence. Selected cysteine mutations were introduced into the DNA coding sequence using the Quickchange Site-Directed Mutagenesis Kit (Stratagene, La Jolla, Calif.). For mutagenesis, polyacrylamide gel-purified oligonucleotides were obtained from Sigma Genosys (Woodlands, Tex.). Transformants were selected, and correct mutational residue changes were verified by DNA sequencing. α-TNTscFv-Cys mutants were expressed in the *E. coli* Tuner strain (Novagen, San Diego Calif.) and purified from the periplasm. α-TNTscFv-Cys mutant samples were labeled with maleimide-activated AlexaFluor 532 dye (AFF 532: quantum yield 0.8, molar extinction coefficient 81 000 $M^{-1}$ $cm^{-1}$; Molecular Probes, Eugene Oreg., with the modification of using 100× less of the dithiothreitol reducing agent. Dye-to-protein ratios of ~1 were obtained. Construction and purification of $(His)_6$-appended myoglobin, with a cysteine mutation at position 64, and its subsequent labeling with Cy3-maleimide (Amersham Bioscience, Piscataway, N.J.). ELISAs for determining TNB binding were performed on the α-TNTscFv-Cys mutants.

Figure 3:
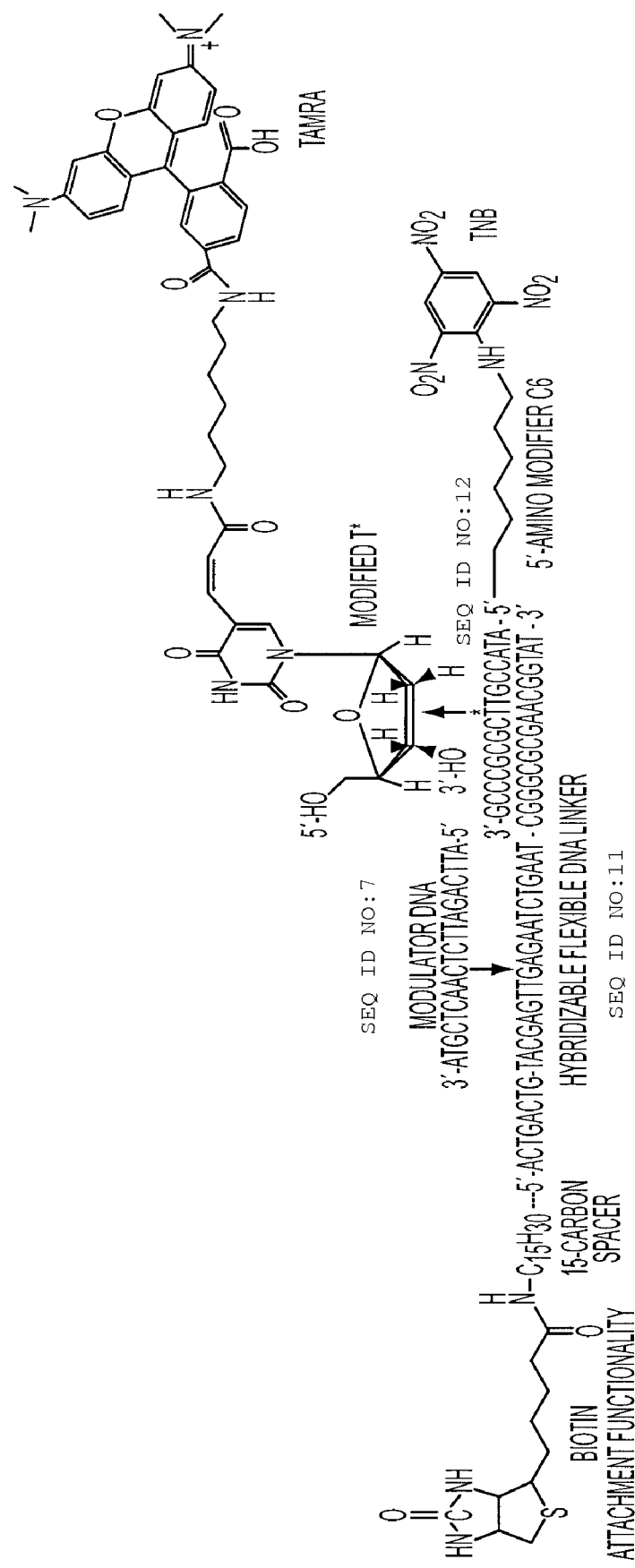
FIG. 3 shows the structure of the dye-labeled TNB DNA arm.

Dye-Labeled TNB DNA Arm: FIG. 3 depicts the dye-labeled TNB DNA arm. The precursor of the dye-labeled TNB DNA arm, purchased from Qiagen (Alameda, Calif.) was already modified with a teramethylrhodamine (TAMRA) dye-labeled internal T* base (quantum yield 0.7, molar extinction coefficient 91 000 $M^{-1}$ $cm^{-1}$) and a 5'-amino modification on a C-6 linker (SEQ. ID. No. 12). The DNA precursor was subsequently reacted with a 1000-fold molar excess of 2,4,6-trinitrobenzene-sulfonic acid (5% solution, Sigma, St. Louis, Mo.), in 1 mL of 0.136 M sodium tetraborate buffer pH 8.5 supplemented with 20 μL of 2 M NaOH. The resulting solution was reacted overnight at room temperature under continuous agitation, then loaded on a Supelclean LC-18 SPE column (Supelco, Bellefonte Pa.), washed with 0.1× borate buffer, and eluted with an increasing concentration of methanol in borate buffer. The mass of the final product (MW ~5878) was verified on an Applied Biosystems API QSTAR Pulsar mass spectrometer by positive electrospray ioniza-tion.

Sensor Assembly: For each well of the Reactibind NA-coated plates (binding capacity ~60 pmol of biotin), 30 pmol of dye-labeled TNB DNA arm was added to 30 pmol of hybridizable flexible DNA linker (SEQ. ID No. 11), heated to 90° C. for 5 min, and then cooled to room temperature slowly to preclude secondary structure formation. The DNA melting temperature is ~62° C. Concurrently, 30 pmol of AlexaFluor 532-labeled α-TNTscFv was mixed with 30 pmol of biotin-X nitrilotriacetic acid tripotassium salt precharged with nickel (Bio-X NTA, Biotium, Hayward Calif., Bio-biotin, X-aminomethoxy spacer, NTA-nitrilotriacetic acid chelator. After 2 hours, DNA and protein solutions were mixed together (now equimolar), diluted with phosphate-buffered saline pH 7.4 (PBS) to a final volume equivalent to 50 μL/well and incubated for 4 h at room temperature. A 50-μL aliquot of sensor solution was added to each well of the NA plates and incubated at 4° C. overnight. For regeneration, sensor-coated plates were washed 10× with 200 μL of PBS and reconstituted in 50 μL of PBS for subsequent retitration. For experiments utilizing modulator DNA, a 1:1 molar ratio of modulator DNA was added to the primary DNA solution (DNA melting temperature is ~55° C.).

Fluorometry and Titration. Fluorometric analysis was performed on a Safire dual monochromator multifunction microtiter plate reader (Tecan, Boston, Mass.). Samples were excited at 510 nm, and emission was recorded at 600 nm. A 5-μL aliquot of 2× solution containing diluted explosive was added to each well at room temperature for 5 minutes to give a final concentration in 100 μL. Each point of a titration was performed in triplicate (three separate wells), and FRET efficiency at 600 nm was monitored during experiments. Titrations are plotted against the change (loss) in fluorescence compared to the 0 concentration point. In the figures, error bars appear where appropriate; if not, the error is within the point value. Approximate binding constants $K_{app}$ were estimated from the second derivative of titration curves and rounded to whole integers.

A homogeneously labeled α-TNTscFv protein and sensor was desirable. Site-specific labeling of proteins is easily accomplished on unique cysteine residues. The current α-TNTscFv protein already contains four cysteines, which are required to form intrachain disulfide bonds to stabilize the variable heavy (VH) and variable light (VL) domains and help maintain the proteins' integrity and recognition function. Since the introduction of additional cysteines could result in detrimental disulfide bond formation during the expression and folding process and a nonfunctional "disulfide scrambled" protein, an intuitive approach based on modeling and design was undertaken. A model was constructed of the α-TNTscFv protein for the determination of optimum mutational sites. Selection criteria included surface-exposed residues to facilitate labeling, proximity to peptide turns, location distal from the binding site, location distal from the already present cysteines, and selection of residues, which, if changed, would have minimal affect on overall structure. The four sites selected were Gln13, Leu145, Ala210, and Ala241. Transformants were obtained for the first three mutational sites. The Ala241 site is proximal to the HISHISHISHISH-ISHISGLYGLYSERGLYGLYHISHISHISHISHISHIS (SEQ ID NO:10), region and this may have interfered with mutagenic oligonucleotide hybridization. After DNA sequence verification of the three mutants obtained, growth and induction revealed that only the strains expressing the α-TNTscFv Ala210Cys and Leu145Cys mutants produced any protein expression. TNB binding was assayed by ELISA, and results indicted that only the α-TNTscFv-Leu145Cys mutant protein had any appreciable TNB binding capacity. This mutant was subsequently dye-labeled with AFF 532 and still retained its TNB binding capacity when reassayed using ELISA.

Sensor Assembly, Titration versus TNT, and Regeneration. The sensor was assembled using the AFF 532-labeled α-TNTscFv-Leu145Cys protein. Attempts at tethering the dye-labeled TNB DNA arm and the labeled protein separately resulted in low amounts of functional sensor assembly; thus, both elements were prebound prior to tethering to the NA surface. This is in contrast to the maltose targeting prototype, which was assembled sequentially. By pre-binding prior to tethering, more active sensor sites consisting of both elements in functional orientations were attached to the surface and available for regeneration after washing. Following sensor self-assembly, TNT in solution was titrated. The resulting loss of FRET-based fluorescence at 600 nm was plotted against the concentration. TNT concentrations higher than 50 mg/L were not used, as TNT solubility in aqueous solutions saturates at concentrations approaching 100 mg/L. A lower limit of detection of 1 mg/L TNT (1 part per million/ppm) was noted for this sensing assembly. The binding curve appears to be a relatively linear function over this series of concentrations tested. The sensor assembly was washed using 10 volumes of 200 μL PBS and then regenerated in 50 μL of PBS for 24 h at 4° C. A second TNT titration was performed, the sensor washed and then regenerated for 1 hour at room temperature, and then a third titration was performed. Similar control experiments performed using sensor assemblies incorporating a dye-labeled DNA arm lacking the TNB moiety or substituting Cy3-labeled myoglobin for the α-TNTscFv resulted in no change in fluorescence upon TNT addition. Additionally, the 600-nm TAMRA emission for these control assemblies was substantially lower, also indicative of inefficient FRET. These results confirm that the same sensor binding of the terminal DNA arm recognition analogue and sensor regeneration performance seen in the maltose sensing prototype is present in the current TNT sensing assembly.

Sensor Specificity and Modulation. To determine specificity and cross-reactivity, sensor assemblies were tested against a variety of TNT structural analogues. Not surprisingly, TNB elicited the highest sensor response in terms of absolute fluorescence change, followed closely by TNT. This result can be attributed to the fact that the antibody fragment was originally selected against TNB and the analogue attached to the DNA arm is also TNB. Thus, TNB will be the most effective competitor for binding sites. RDX and 2-A-4,6-DNT caused significantly less response, with 2,4-DNT eliciting the least response. Since 2-A-4,6-DNT elicits all of its response between 5 and 20 mg/L, the result is almost a complete "classical" binding curve in comparison to the results elicited from the other explosive compounds. It should be noted that, in this format, TNT cannot be distinguished from the structurally related competitors until higher concentrations. As mentioned, issues of solubility limit the concentration range that can be tested for these compounds, limiting them to the "linear" portion of the curve. Nevertheless, these results very closely parallel the competition ELISA format used to test the precursor anti-TNB scFv selected. This demonstrates that the original α-TNTscFv specificity is retained even after multiple modifications including the following: (1) appending a $(His)_6$-spacer-$(His)_6$, (2) point mutation to a cysteine, (3) dye labeling of the cysteine, (4) surface tethering, and (5) interacting with the dye-labeled TNB DNA arm as part of sensing. This also parallels the specificity retained by the maltose sensing prototype after similar modifications.

The dynamic sensing range of the maltose sensing prototype could be modulated by "stiffening" of the tether arm through the addition of a DNA complementary to the DNA linker. Although the binding constant essentially remained the same, the binding curve of the modulated prototype became broader, significantly increasing the useful sensing range. Similar experiments were performed with the current TNT sensing assembly. During self-assembly, modulator DNA was added to the hybridizable flexible DNA linker, significantly increasing the amount of double-stranded DNA from 16 of 44 bases (~35%) in the unmodulated sensor to 36/44 (~80%) when modulated. The lower limit of TNT detection of the modulated sensor dropped ~10-fold from 1 to 0.1 mg/mL (1 ppm to 100 parts per billion/ppb). In parallel to the prototype, these results show that the modulation mechanism can be exploited to adjust useful sensor properties. The choice of C6 chain, 5'-amino-C6 and 15-carbon spacer in the DNA arm was driven by availability for incorporation during automated DNA synthesis. It should be noted that adjusting the length of the single-stranded DNA arm (as opposed to rigidity) in the maltose sensing prototype did not effect binding properties. Thus, adjusting these alkane moieties in terms of length were not considered critical in the current sensor as well. "Switching in" of a more sensitive scFv antibody fragment would be another mechanism of adjusting sensor properties.

The TNT sensing assembly demonstrated retains almost all of the desirable properties of the MBP-based prototype while targeting a different analyte. Among the useful features of this sensor are the use of robust avidin-biotin technology for surface tethering and the ease of self-assembly in a microtiter plate format, which also facilitates analysis by readily accessible fluorescent plate readers. The prototype and current sensor use dye-based FRET; however, signal transduction may be expanded to other proximity-sensitive methods such as electrochemical detection. The choices of FRET dyes and their locations on either module are also interchangeable, which can allow optimization to address any potential distance requirements. Furthermore, the sensor can be regenerated for subsequent reuse. In these experiments, an upper limit of 6-8 regenerations was obtained. Regeneration in less than 1 hour is feasible. Sensor response in the current microtiter well format is limited by technician handling time, which suggests that real-time sensing in a flow cell is feasible.

The modularity of the sensor design disclosed is demonstrated by readily adapting it to target another analyte. As such, the sensitivity of the biorecognition element was not a major criterion. However, this does not preclude the current sensor from actual use as a solution-phase TNT sensor. More sensitive $(His)_6$-appended TNT recognition elements are available that demonstrate nanomolar sensitivity. The current α-TNTscFv fragment could undergo another round of evolution to select for higher affinity mutants. Although the modulated behavior of the sensor was modest, 10-fold decrease in limit of detection, the conservation of this feature seen is important. The addition of DNA to stiffen the arm creates sensors that are more sensitive to perturbation, thus increasing sensitivity and yielding a lower limit of detection. Due to the issues of TNT solubility, the same broadening of the dynamic sensing range with DNA stiffening could not be fully tested. However, this result suggests that modulation through careful control of arm stiffness/kinetics can be further exploited to yield sensing assemblies with variable control over the desired affinities. The combination of "switching in" of mutant proteins with different affinities and sensor arm modulation may also potentiate the sensitivity attainable.

The modular nature and adaptability of this sensor design can easily be adapted to target another analyte and yet remain functionally robust. Choices of biorecognition elements that can fit directly into the current format include $(His)_6$-appended proteins such as bPBPs, scFv fragments, or even soluble fragments of cloned cellular receptors. The $(His)_6$ motif is commonly engineered into many cloned proteins for facile purification over Ni-NTA media. Additionally, an analogue of the primary analyte of interest must be attached to the distal end of the DNA arm and many covalent and noncovalent chemical linking strategies are known in the art to address this. A variety of choices are available for both the biorecognition module and the modular arm. Adaptation of this sensor for testing in a drug discovery assay where a variety of compounds with differing affinities for the biorecognition module can be screened in parallel is possible. Multianalyte or "multiplex" sensing is another possibility. Other applications may include providing a variety of sensors in a microtiter well format for screening or quantitation of many different analytes such as in a clinical setting. Sensor assemblies can be dried, stored, and reconstituted for later use. This suggested that sensors could be assembled on microtiter plates and dried/stored for later use in other locations. Although demonstrated in a microtiter well plate format, assembly of these sensors in flow cells and on other surfaces, including nanoparticle surfaces, is possible.

Obviously, many modifications and variations of the present invention are possible in light of the above teachings. It is therefore to be understood that, within the scope of the appended claims, the invention may be practiced otherwise than as specifically described.

What is claimed is:

1. A modular biosensor comprising:
a biorecognition element, comprising a biorecognition module, said biorecognition module being labeled with a first signaling module;
a modular arm element, comprising of a flexible arm and a recognition module, wherein said modular arm element is labeled with a second signaling module, wherein said modular arm element is specifically oriented in reference to the biorecognition element, wherein said biorecognition element is linked to said modular arm element, wherein said biorecognition module and said recognition module of said modular arm element bind, wherein said first and second signaling modules are in close proximity to each other to establish a baseline fluorescence resonance energy transfer (FRET); and
a detector for detecting a change in FRET,
wherein the biorecognition element and the modular arm element are immobilized on a surface.

2. The modular biosensor of claim 1, wherein said biorecognition element is linked to said modular arm element either covalently or non-covalently.

3. The biosensor of claim 1, wherein said signaling module is a dye, a quencher, an electrochemically active group, a quantum dot or an enzyme.

4. The biosensor of claim 1, wherein said biorecognition module is a protein, an enzyme, a receptor, a bacterial periplasmic binding protein, an antibody fragment, a peptide, an aptamer, a carbohydrate, DNA, PNA, RNA, or other macromolecule.

5. The biosensor of claim 1, wherein said biorecognition module is at least one protein, an enzyme, a receptor, a bacterial periplasmic binding protein, an antibody fragment, a peptide, an aptamer, a carbohydrate, DNA, PNA, RNA, or other macromolecule.

6. The biosensor of claim 1, wherein the flexible arm is comprised of a SS-DNA, a DS-DNA, a combination of a SS-DNA and a DS-DNA, a thiolated DNA, a RNA, a thiolated RNA, a linear homopolymer, a linear copolymer, a block copolymer, a PNA, an α peptides, a β peptides, a protein, a polymer, or an oligosaccharide.

7. The biosensor of claim 1, wherein the recognition module is comprised of at least one antigen, epitope, analyte, substrate, protein, peptide, toxin, sugar, biological agent, or analogs of said antigen, epitope, analyte, substrate, protein, peptide, toxin, sugar, or biological agent.

8. The modular biosensor of claim 1, wherein said biorecognition element is attached to a surface by a surface attachment module by surface attachment.

9. The biosensor of claim 8, wherein said surface attachment module is comprised of biotin, avidin, antibody, reactive thiol, reactive amine, non-reversible enzyme substrate, protein A, protein G, protein L, DS-DNA, or PNA.

10. The biosensor of claim 8, wherein said surface attachment is biotin-avidin chemistry, metal-affinity coordination, thiol bonding, hydrophobic interactions, or DNA-directed immobilization.

11. The biosensor of claim 8, wherein said surface is comprised of a polystyrene micro-titer plate well, a solid planar macromaterial, a spherical or other shaped material, a microscopic planar, spherical or other shaped micro- or nanomaterial, a nanocrystalline, a modified nanocrystalline material, a molecular or biomolecular assembly composed of protein, DNA, RNA, PNA, morpholine DNA, or other biomolecule and their derivatives, a molecularly templated material, a polymer, or a mineral.

12. The biosensor of claim 1, wherein said biorecognition element and said modular arm element have a specific binding affinity.

13. The biosensor of claim 12, wherein said specific binding affinity is modulated by altering said biorecognition module.

14. The biosensor of claim 12, wherein said specific binding affinity is modulated by temperature.

15. The biosensor of claim 12, wherein said specific binding affinity is modulated by altering the properties of the flexible arm of the modular arm element.

16. A method of making a modular biosensor according to claim 1, comprising the steps of:
providing the biorecognition module;
labeling the biorecognition module with the signaling module;
synthesizing the modular arm element;
labeling the modular arm element with the signaling module;
linking the biorecognition module to the modular arm element; and
binding the biorecognition module and the modular arm element by self assembly to establish the modular biosensor according to claim 1.

17. A method of making a modular biosensor according to claim 1 on a surface, comprising the steps of:

providing the biorecognition module;
labeling the biorecognition module;
synthesizing the modular arm element;
labeling the modular arm element;
attaching the biorecognition module and the modular arm element to the surface; and
binding the biorecognition module and the modular arm element by self assembly to establish the modular biosensor according to claim 1.

18. A method of making a modular biosensor according to claim 1 on a surface, comprising the steps of:
providing the biorecognition module;
labeling the biorecognition module;
synthesizing the modular arm element;
labeling the modular arm element;
binding the biorecognition module and the modular arm element by self assembly to establish the modular biosensor according to claim 1; and
attaching the modular biosensor to a the surface.

19. A biosensor array comprising a plurality of biosensors according to claim 1, wherein at least one of the plurality of biosensors is the modular biosensor according to claim 1.

20. A sensor array according to claim 19, wherein each of the biosensors is the modular biosensor according to claim 1.

* * * * *